US012644147B2

(12) United States Patent
Liang et al.

(10) Patent No.: US 12,644,147 B2
(45) Date of Patent: Jun. 2, 2026

(54) METHOD FOR MULTIPLEX NUCLEIC ACID DETECTION BASED ON CLUSTERED REGULARLY INTERSPACED SHORT PALINDROMIC REPEAT

(71) Applicant: SHANDONG SHUNFENG BIOTECHNOLOGY CO., LTD., Jinan (CN)

(72) Inventors: Yafeng Liang, Jinan (CN); Jie Sun, Jinan (CN); Ruiheng Liu, Jinan (CN)

(73) Assignee: SHANDONG SHUNFENG BIOTECHNOLOGY CO., LTD., Jinan (CN)

( * ) Notice: Subject to any disclaimer, the term of this patent is extended or adjusted under 35 U.S.C. 154(b) by 1173 days.

(21) Appl. No.: 17/648,180

(22) Filed: Jan. 18, 2022

(65) Prior Publication Data

US 2022/0136075 A1     May 5, 2022

Related U.S. Application Data

(63) Continuation of application No. PCT/CN2021/114374, filed on Aug. 24, 2021.

(30) Foreign Application Priority Data

Aug. 28, 2020    (CN) .......................... 202010888036.3
Mar. 3, 2021    (CN) .......................... 202110236947.2

(51) Int. Cl.
*C12Q 1/6816*      (2018.01)
*C12N 9/22*      (2006.01)
*C12N 15/11*      (2006.01)
*C12N 15/113*      (2010.01)
*C12Q 1/70*      (2006.01)

(52) U.S. Cl.
CPC ............. *C12Q 1/6816* (2013.01); *C12N 9/22* (2013.01); *C12N 15/111* (2013.01); *C12N 15/113* (2013.01); *C12Q 1/701* (2013.01);

*C12N 2310/20* (2017.05); *C12Q 2521/307* (2013.01); *C12Q 2525/113* (2013.01); *C12Q 2525/119* (2013.01)

(58) Field of Classification Search
CPC ............ C12Q 1/6876; C12Q 2525/113; C12Q 2525/119; C12N 2310/20; C12N 15/113
See application file for complete search history.

(56) References Cited

U.S. PATENT DOCUMENTS 8,153,772 B2     4/2012   Brown et al.
2022/0267847 A1*   8/2022   Wang ................... C12Q 1/6823

FOREIGN PATENT DOCUMENTS

CN      101454451 A     6/2009
WO      2019104058 A1     5/2019

OTHER PUBLICATIONS

Winston X. Yan, et al., Functionally diverse type V CRISPR-Cas systems, Science, 2018, pp. 1-8.
Patrick Pausch, et al., CRISPR-Cas from huge phages is a hypercompact genome editor, Science, 2020, pp. 333-337, vol. 369, No. 6501.

* cited by examiner

*Primary Examiner* — Sarae L Bausch
(74) *Attorney, Agent, or Firm* — Bayramoglu Law Offices LLC

(57)     ABSTRACT

A method for multiplex nucleic acid detection based on clustered regularly interspaced short palindromic repeat (CRISPR), a system, and a kit for detecting a target nucleic acid based on CRISPR are provided. The detection method includes: adding any one, any two, any three, or four from the group consisting of a first nucleic acid detection composition, a second nucleic acid detection composition, a third nucleic acid detection composition, and a fourth nucleic acid detection composition to a reaction system with a target nucleic acid to achieve the multiplex detection of the target nucleic acid.

20 Claims, 5 Drawing Sheets

Specification includes a Sequence Listing.

SEQUENCE LISTING

<160> NUMBER OF SEQ ID NOS: 19

<210> SEQ ID NO 1
<211> LENGTH: 1228
<212> TYPE: PRT
<213> ORGANISM: Artificial Sequence
<220> FEATURE:
<223> OTHER INFORMATION: LbCas12a

<400> SEQUENCE: 1

```
Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
            35                  40                  45

Gly Val Lys Lys Leu Leu Asp Arg Tyr Tyr Leu Ser Phe Ile Asn Asp
        50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
            115                 120                 125

Pro Glu Phe Leu Asp Asp Lys Asp Glu Ile Ala Leu Val Asn Ser Phe
        130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
            195                 200                 205

Ile Leu Asn Ser Asp Tyr Asp Val Glu Asp Phe Phe Glu Gly Glu Phe
        210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
            275                 280                 285

Phe Tyr Gly Glu Gly Tyr Thr Ser Asp Glu Glu Val Leu Glu Val Phe
        290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
```

-continued

```
            355                 360                 365

Ile His Leu Lys Lys Lys Ala Val Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
                420                 425                 430

Glu Lys Leu Phe Asp Ala Asp Phe Val Leu Glu Lys Ser Leu Lys Lys
        435                 440                 445

Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
        515                 520                 525

Gln Phe Met Gly Gly Trp Asp Lys Asp Lys Glu Thr Asp Tyr Arg Ala
    530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
            595                 600                 605

Ser Glu Asp Ile Gln Lys Ile Tyr Lys Asn Gly Thr Phe Lys Lys Gly
        610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
        675                 680                 685

Glu Val Asp Lys Leu Val Glu Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
        755                 760                 765

Asn Pro Asp Asn Pro Lys Lys Thr Thr Thr Leu Ser Tyr Asp Val Tyr
    770                 775                 780
```

```
Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
            820                 825                 830

Arg Gly Glu Arg Asn Leu Leu Tyr Ile Val Val Val Asp Gly Lys Gly
        835                 840                 845

Asn Ile Val Glu Gln Tyr Ser Leu Asn Glu Ile Ile Asn Asn Phe Asn
    850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
            885                 890                 895

Lys Glu Leu Lys Ala Gly Tyr Ile Ser Gln Val Val His Lys Ile Cys
        900                 905                 910

Glu Leu Val Glu Lys Tyr Asp Ala Val Ile Ala Leu Glu Asp Leu Asn
        915                 920                 925

Ser Gly Phe Lys Asn Ser Arg Val Lys Val Glu Lys Gln Val Tyr Gln
    930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
            965                 970                 975

Thr Asn Lys Phe Glu Ser Phe Lys Ser Met Ser Thr Gln Asn Gly Phe
            980                 985                 990

Ile Phe Tyr Ile Pro Ala Trp Leu  Thr Ser Lys Ile Asp  Pro Ser Thr
        995                 1000                1005

Gly Phe Val Asn Leu Leu Lys  Thr Lys Tyr Thr Ser  Ile Ala Asp
    1010                1015                1020

Ser Lys Lys Phe Ile Ser Ser  Phe Asp Arg Ile Met  Tyr Val Pro
    1025                1030                1035

Glu Glu Asp Leu Phe Glu Phe  Ala Leu Asp Tyr Lys  Asn Phe Ser
    1040                1045                1050

Arg Thr Asp Ala Asp Tyr Ile  Lys Lys Trp Lys Leu  Tyr Ser Tyr
    1055                1060                1065

Gly Asn Arg Ile Arg Ile Phe  Arg Asn Pro Lys Lys  Asn Asn Val
    1070                1075                1080

Phe Asp Trp Glu Glu Val Cys  Leu Thr Ser Ala Tyr  Lys Glu Leu
    1085                1090                1095

Phe Asn Lys Tyr Gly Ile Asn  Tyr Gln Gln Gly Asp  Ile Arg Ala
    1100                1105                1110

Leu Leu Cys Glu Gln Ser Asp  Lys Ala Phe Tyr Ser  Ser Phe Met
    1115                1120                1125

Ala Leu Met Ser Leu Met Leu  Gln Met Arg Asn Ser  Ile Thr Gly
    1130                1135                1140

Arg Thr Asp Val Asp Phe Leu  Ile Ser Pro Val Lys  Asn Ser Asp
    1145                1150                1155

Gly Ile Phe Tyr Asp Ser Arg  Asn Tyr Glu Ala Gln  Glu Asn Ala
    1160                1165                1170

Ile Leu Pro Lys Asn Ala Asp  Ala Asn Gly Ala Tyr  Asn Ile Ala
    1175                1180                1185
```

-continued

```
Arg Lys  Val Leu Trp Ala Ile  Gly Gln Phe Lys Lys  Ala Glu Asp
    1190             1195             1200

Glu Lys  Leu Asp Lys Val Lys  Ile Ala Ile Ser Asn  Lys Glu Trp
    1205             1210             1215

Leu Glu  Tyr Ala Gln Thr Ser  Val Lys His
    1220             1225

<210> SEQ ID NO 2
<211> LENGTH: 1129
<212> TYPE: PRT
<213> ORGANISM: Artificial Sequence
<220> FEATURE:
<223> OTHER INFORMATION: Cas12b

<400> SEQUENCE: 2

Met Ala Val Lys Ser Ile Lys Val Lys Leu Arg Leu Asp Asp Met Pro
1               5                  10                  15

Glu Ile Arg Ala Gly Leu Trp Lys Leu His Lys Glu Val Asn Ala Gly
            20                  25                  30

Val Arg Tyr Tyr Thr Glu Trp Leu Ser Leu Leu Arg Gln Glu Asn Leu
        35                  40                  45

Tyr Arg Arg Ser Pro Asn Gly Asp Gly Glu Gln Glu Cys Asp Lys Thr
    50                  55                  60

Ala Glu Glu Cys Lys Ala Glu Leu Leu Glu Arg Leu Arg Ala Arg Gln
65                  70                  75                  80

Val Glu Asn Gly His Arg Gly Pro Ala Gly Ser Asp Asp Glu Leu Leu
                85                  90                  95

Gln Leu Ala Arg Gln Leu Tyr Glu Leu Leu Val Pro Gln Ala Ile Gly
            100                 105                 110

Ala Lys Gly Asp Ala Gln Gln Ile Ala Arg Lys Phe Leu Ser Pro Leu
            115                 120                 125

Ala Asp Lys Asp Ala Val Gly Gly Leu Gly Ile Ala Lys Ala Gly Asn
    130                 135                 140

Lys Pro Arg Trp Val Arg Met Arg Glu Ala Gly Glu Pro Gly Trp Glu
145                 150                 155                 160

Glu Glu Lys Glu Lys Ala Glu Thr Arg Lys Ser Ala Asp Arg Thr Ala
            165                 170                 175

Asp Val Leu Arg Ala Leu Ala Asp Phe Gly Leu Lys Pro Leu Met Arg
            180                 185                 190

Val Tyr Thr Asp Ser Glu Met Ser Ser Val Glu Trp Lys Pro Leu Arg
        195                 200                 205

Lys Gly Gln Ala Val Arg Thr Trp Asp Arg Asp Met Phe Gln Gln Ala
    210                 215                 220

Ile Glu Arg Met Met Ser Trp Glu Ser Trp Asn Gln Arg Val Gly Gln
225                 230                 235                 240

Glu Tyr Ala Lys Leu Val Glu Gln Lys Asn Arg Phe Glu Gln Lys Asn
            245                 250                 255

Phe Val Gly Gln Glu His Leu Val His Leu Val Asn Gln Leu Gln Gln
            260                 265                 270

Asp Met Lys Glu Ala Ser Pro Gly Leu Glu Ser Lys Glu Gln Thr Ala
            275                 280                 285

His Tyr Val Thr Gly Arg Ala Leu Arg Gly Ser Asp Lys Val Phe Glu
    290                 295                 300

Lys Trp Gly Lys Leu Ala Pro Asp Ala Pro Phe Asp Leu Tyr Asp Ala
305                 310                 315                 320
```

Glu Ile Lys Asn Val Gln Arg Arg Asn Thr Arg Arg Phe Gly Ser His
                325                     330                 335

Asp Leu Phe Ala Lys Leu Ala Glu Pro Glu Tyr Gln Ala Leu Trp Arg
            340                 345                 350

Glu Asp Ala Ser Phe Leu Thr Arg Tyr Ala Val Tyr Asn Ser Ile Leu
            355                 360                 365

Arg Lys Leu Asn His Ala Lys Met Phe Ala Thr Phe Thr Leu Pro Asp
        370                 375                 380

Ala Thr Ala His Pro Ile Trp Thr Arg Phe Asp Lys Leu Gly Gly Asn
385                 390                 395                 400

Leu His Gln Tyr Thr Phe Leu Phe Asn Glu Phe Gly Glu Arg Arg His
                405                 410                 415

Ala Ile Arg Phe His Lys Leu Leu Lys Val Glu Asn Gly Val Ala Arg
                420                 425                 430

Glu Val Asp Asp Val Thr Val Pro Ile Ser Met Ser Glu Gln Leu Asp
            435                 440                 445

Asn Leu Leu Pro Arg Asp Pro Asn Glu Pro Ile Ala Leu Tyr Phe Arg
        450                 455                 460

Asp Tyr Gly Ala Glu Gln His Phe Thr Gly Glu Phe Gly Gly Ala Lys
465                 470                 475                 480

Ile Gln Cys Arg Arg Asp Gln Leu Ala His Met His Arg Arg Arg Gly
                485                 490                 495

Ala Arg Asp Val Tyr Leu Asn Val Ser Val Arg Val Gln Ser Gln Ser
                500                 505                 510

Glu Ala Arg Gly Glu Arg Arg Pro Pro Tyr Ala Ala Val Phe Arg Leu
            515                 520                 525

Val Gly Asp Asn His Arg Ala Phe Val His Phe Asp Lys Leu Ser Asp
        530                 535                 540

Tyr Leu Ala Glu His Pro Asp Asp Gly Lys Leu Gly Ser Glu Gly Leu
545                 550                 555                 560

Leu Ser Gly Leu Arg Val Met Ser Val Asp Leu Gly Leu Arg Thr Ser
                565                 570                 575

Ala Ser Ile Ser Val Phe Arg Val Ala Arg Lys Asp Glu Leu Lys Pro
            580                 585                 590

Asn Ser Lys Gly Arg Val Pro Phe Phe Phe Pro Ile Lys Gly Asn Asp
        595                 600                 605

Asn Leu Val Ala Val His Glu Arg Ser Gln Leu Leu Lys Leu Pro Gly
        610                 615                 620

Glu Thr Glu Ser Lys Asp Leu Arg Ala Ile Arg Glu Glu Arg Gln Arg
625                 630                 635                 640

Thr Leu Arg Gln Leu Arg Thr Gln Leu Ala Tyr Leu Arg Leu Leu Val
                645                 650                 655

Arg Cys Gly Ser Glu Asp Val Gly Arg Arg Glu Arg Ser Trp Ala Lys
            660                 665                 670

Leu Ile Glu Gln Pro Val Asp Ala Ala Asn His Met Thr Pro Asp Trp
            675                 680                 685

Arg Glu Ala Phe Glu Asn Glu Leu Gln Lys Leu Lys Ser Leu His Gly
        690                 695                 700

Ile Cys Ser Asp Lys Glu Trp Met Asp Ala Val Tyr Glu Ser Val Arg
705                 710                 715                 720

Arg Val Trp Arg His Met Gly Lys Gln Val Arg Asp Trp Arg Lys Asp
                725                 730                 735

Val Arg Ser Gly Glu Arg Pro Lys Ile Arg Gly Tyr Ala Lys Asp Val

-continued

```
              740              745              750

Val Gly Gly Asn Ser Ile Glu Gln Ile Glu Tyr Leu Glu Arg Gln Tyr
        755              760              765

Lys Phe Leu Lys Ser Trp Ser Phe Phe Gly Lys Val Ser Gly Gln Val
    770              775              780

Ile Arg Ala Glu Lys Gly Ser Arg Phe Ala Ile Thr Leu Arg Glu His
785              790              795              800

Ile Asp His Ala Lys Glu Asp Arg Leu Lys Lys Leu Ala Asp Arg Ile
            805              810              815

Ile Met Glu Ala Leu Gly Tyr Val Tyr Ala Leu Asp Glu Arg Gly Lys
            820              825              830

Gly Lys Trp Val Ala Lys Tyr Pro Pro Cys Gln Leu Ile Leu Leu Glu
            835              840              845

Glu Leu Ser Glu Tyr Gln Phe Asn Asn Asp Arg Pro Pro Ser Glu Asn
        850              855              860

Asn Gln Leu Met Gln Trp Ser His Arg Gly Val Phe Gln Glu Leu Ile
865              870              875              880

Asn Gln Ala Gln Val His Asp Leu Leu Val Gly Thr Met Tyr Ala Ala
            885              890              895

Phe Ser Ser Arg Phe Asp Ala Arg Thr Gly Ala Pro Gly Ile Arg Cys
            900              905              910

Arg Arg Val Pro Ala Arg Cys Thr Gln Glu His Asn Pro Glu Pro Phe
            915              920              925

Pro Trp Trp Leu Asn Lys Phe Val Val Glu His Thr Leu Asp Ala Cys
    930              935              940

Pro Leu Arg Ala Asp Asp Leu Ile Pro Thr Gly Glu Gly Glu Ile Phe
945              950              955              960

Val Ser Pro Phe Ser Ala Glu Glu Gly Asp Phe His Gln Ile His Ala
            965              970              975

Asp Leu Asn Ala Ala Gln Asn Leu Gln Gln Arg Leu Trp Ser Asp Phe
        980              985              990

Asp Ile Ser Gln Ile Arg Leu Arg Cys Asp Trp Gly Glu Val Asp Gly
        995              1000             1005

Glu Leu Val Leu Ile Pro Arg Leu Thr Gly Lys Arg Thr Ala Asp
    1010             1015             1020

Ser Tyr Ser Asn Lys Val Phe Tyr Thr Asn Thr Gly Val Thr Tyr
    1025             1030             1035

Tyr Glu Arg Glu Arg Gly Lys Lys Arg Arg Lys Val Phe Ala Gln
    1040             1045             1050

Glu Lys Leu Ser Glu Glu Glu Ala Glu Leu Leu Val Glu Ala Asp
    1055             1060             1065

Glu Ala Arg Glu Lys Ser Val Val Leu Met Arg Asp Pro Ser Gly
    1070             1075             1080

Ile Ile Asn Arg Gly Asn Trp Thr Arg Gln Lys Glu Phe Trp Ser
    1085             1090             1095

Met Val Asn Gln Arg Ile Glu Gly Tyr Leu Val Lys Gln Ile Arg
    1100             1105             1110

Ser Arg Val Pro Leu Gln Asp Ser Ala Cys Glu Asn Thr Gly Asp
    1115             1120             1125

Ile
```

<210> SEQ ID NO 3
<211> LENGTH: 1045

-continued

<212> TYPE: PRT
<213> ORGANISM: Artificial Sequence
<220> FEATURE:
<223> OTHER INFORMATION: Cas12i
<400> SEQUENCE: 3

```
Met Lys Lys Val Glu Val Ser Arg Pro Tyr Gln Ser Leu Leu Leu Pro
1               5                   10                  15

Asn His Arg Lys Phe Lys Tyr Leu Asp Glu Thr Trp Asn Ala Tyr Lys
            20                  25                  30

Ser Val Lys Ser Leu Leu His Arg Phe Leu Val Cys Ala Tyr Gly Ala
            35                  40                  45

Val Pro Phe Asn Lys Phe Val Glu Val Val Glu Lys Val Asp Asn Asp
        50                  55                  60

Gln Leu Val Leu Ala Phe Ala Val Arg Leu Phe Arg Leu Val Pro Val
65                  70                  75                  80

Glu Ser Thr Ser Phe Ala Lys Val Asp Lys Ala Asn Leu Ala Lys Ser
                85                  90                  95

Leu Ala Asn His Leu Pro Val Gly Thr Ala Ile Pro Ala Asn Val Gln
            100                 105                 110

Ser Tyr Phe Asp Ser Asn Phe Asp Pro Lys Lys Tyr Met Trp Ile Asp
        115                 120                 125

Cys Ala Trp Glu Ala Asp Arg Leu Ala Arg Glu Met Gly Leu Ser Ala
        130                 135                 140

Ser Gln Phe Ser Glu Tyr Ala Thr Thr Met Leu Trp Glu Asp Trp Leu
145                 150                 155                 160

Pro Leu Asn Lys Asp Asp Val Asn Gly Trp Gly Ser Val Ser Gly Leu
            165                 170                 175

Phe Gly Glu Gly Lys Lys Glu Asp Arg Gln Gln Lys Val Lys Met Leu
            180                 185                 190

Asn Asn Leu Leu Asn Gly Ile Lys Lys Asn Pro Pro Lys Asp Tyr Thr
            195                 200                 205

Gln Tyr Leu Lys Ile Leu Leu Asn Ala Phe Asp Ala Lys Ser His Lys
        210                 215                 220

Glu Ala Val Lys Asn Tyr Lys Gly Asp Ser Thr Gly Arg Thr Ala Ser
225                 230                 235                 240

Tyr Leu Ser Glu Lys Ser Gly Glu Ile Thr Glu Leu Met Leu Glu Gln
            245                 250                 255

Leu Met Ser Asn Ile Gln Arg Asp Ile Gly Asp Lys Gln Lys Glu Ile
            260                 265                 270

Ser Leu Pro Lys Lys Asp Val Val Lys Lys Tyr Leu Glu Ser Glu Ser
        275                 280                 285

Gly Val Pro Tyr Asp Gln Asn Leu Trp Ser Gln Ala Tyr Arg Asn Ala
        290                 295                 300

Ala Ser Ser Ile Lys Lys Thr Asp Thr Arg Asn Phe Asn Ser Thr Leu
305                 310                 315                 320

Glu Lys Phe Lys Asn Glu Val Glu Leu Arg Gly Leu Leu Ser Glu Gly
            325                 330                 335

Asp Asp Val Glu Ile Leu Arg Ser Lys Phe Phe Ser Ser Glu Phe His
            340                 345                 350

Lys Thr Pro Asp Lys Phe Val Ile Lys Pro Glu His Ile Gly Phe Asn
        355                 360                 365

Asn Lys Tyr Asn Val Val Ala Glu Leu Tyr Lys Leu Lys Ala Glu Ala
        370                 375                 380
```

```
Thr Asp Phe Glu Ser Ala Phe Ala Thr Val Lys Asp Glu Phe Glu Glu
385                 390                 395                 400

Lys Gly Ile Lys His Pro Ile Lys Asn Ile Leu Glu Tyr Ile Trp Asn
                405                 410                 415

Asn Glu Val Pro Val Glu Lys Trp Gly Arg Val Ala Arg Phe Asn Gln
                420                 425                 430

Ser Glu Glu Lys Leu Leu Arg Ile Lys Ala Asn Pro Thr Val Glu Cys
                435                 440                 445

Asn Gln Gly Met Thr Phe Gly Asn Ser Ala Met Val Gly Glu Val Leu
        450                 455                 460

Arg Ser Asn Tyr Val Ser Lys Lys Gly Ala Leu Val Ser Gly Glu His
465                 470                 475                 480

Gly Gly Arg Leu Ile Gly Gln Asn Asn Met Ile Trp Leu Glu Met Arg
                485                 490                 495

Leu Leu Asn Lys Gly Lys Trp Glu Thr His His Val Pro Thr His Asn
                500                 505                 510

Met Lys Phe Phe Glu Glu Val His Ala Tyr Asn Pro Ser Leu Ala Asp
        515                 520                 525

Ser Val Asn Val Arg Asn Arg Leu Tyr Arg Ser Glu Asp Tyr Thr Gln
        530                 535                 540

Leu Pro Ser Ser Ile Thr Asp Gly Leu Lys Gly Asn Pro Lys Ala Lys
545                 550                 555                 560

Leu Leu Lys Arg Gln His Cys Ala Leu Asn Asn Met Thr Ala Asn Val
                565                 570                 575

Leu Asn Pro Lys Leu Ser Phe Thr Ile Asn Lys Lys Asn Asp Asp Tyr
                580                 585                 590

Thr Val Ile Ile Val His Ser Val Glu Val Ser Lys Pro Arg Arg Glu
                595                 600                 605

Val Leu Val Gly Asp Tyr Leu Val Gly Met Asp Gln Asn Gln Thr Ala
        610                 615                 620

Ser Asn Thr Tyr Ala Val Met Gln Val Val Lys Pro Lys Ser Thr Asp
625                 630                 635                 640

Ala Ile Pro Phe Arg Asn Met Trp Val Arg Phe Val Glu Ser Gly Ser
                645                 650                 655

Ile Glu Ser Arg Thr Leu Asn Ser Arg Gly Glu Tyr Val Asp Gln Leu
                660                 665                 670

Asn His Asp Gly Val Asp Leu Phe Glu Ile Gly Asp Thr Glu Trp Val
        675                 680                 685

Asp Ser Ala Arg Lys Phe Phe Asn Lys Leu Gly Val Lys His Lys Asp
        690                 695                 700

Gly Thr Leu Val Asp Leu Ser Thr Ala Pro Arg Lys Ala Tyr Ala Phe
705                 710                 715                 720

Asn Asn Phe Tyr Phe Lys Thr Met Leu Asn His Leu Arg Ser Asn Glu
                725                 730                 735

Val Asp Leu Thr Leu Leu Arg Asn Glu Ile Leu Arg Val Ala Asn Gly
                740                 745                 750

Arg Phe Ser Pro Met Arg Leu Gly Ser Leu Ser Trp Thr Thr Leu Lys
                755                 760                 765

Ala Leu Gly Ser Phe Lys Ser Leu Val Leu Ser Tyr Phe Asp Arg Leu
        770                 775                 780

Gly Ala Lys Glu Met Val Asp Lys Glu Ala Lys Asp Lys Ser Leu Phe
785                 790                 795                 800

Asp Leu Leu Val Ala Ile Asn Asn Lys Arg Ser Asn Lys Arg Glu Glu
```

```
                 805               810               815
Arg Thr Ser Arg Ile Ala Ser Ser Leu Met Thr Val Ala Gln Lys Tyr
            820               825               830

Lys Val Asp Asn Ala Val Val His Val Val Val Glu Gly Asn Leu Ser
            835               840               845

Ser Thr Asp Arg Ser Ala Ser Lys Ala His Asn Arg Asn Thr Met Asp
        850               855               860

Trp Cys Ser Arg Ala Val Val Lys Lys Leu Glu Asp Met Cys Asn Leu
865               870               875               880

Tyr Gly Phe Asn Ile Lys Gly Val Pro Ala Phe Tyr Thr Ser His Gln
                885               890               895

Asp Pro Leu Val His Arg Ala Asp Tyr Asp Asp Pro Lys Pro Ala Leu
            900               905               910

Arg Cys Arg Tyr Ser Ser Tyr Ser Arg Ala Asp Phe Ser Lys Trp Gly
            915               920               925

Gln Asn Ala Leu Ala Ala Val Val Arg Trp Ala Ser Asn Lys Lys Ser
        930               935               940

Asn Thr Cys Tyr Lys Val Gly Ala Val Glu Phe Leu Lys Gln His Gly
945               950               955               960

Leu Phe Ala Asp Lys Lys Leu Thr Val Glu Gln Phe Leu Ser Lys Val
                965               970               975

Lys Asp Glu Glu Ile Leu Ile Pro Arg Arg Gly Gly Arg Val Phe Leu
            980               985               990

Thr Thr His Arg Leu Leu Ala Glu Ser Thr Phe Val Tyr Leu Asn Gly
            995              1000              1005

Val Lys Tyr His Ser Cys Asn Ala Asp Glu Val Ala Ala Val Asn
    1010              1015              1020

Ile Cys Leu Asn Asp Trp Val Ile Pro Cys Lys Lys Lys Met Lys
    1025              1030              1035

Glu Glu Ser Ser Ala Ser Gly
    1040              1045

<210> SEQ ID NO 4
<211> LENGTH: 908
<212> TYPE: PRT
<213> ORGANISM: Artificial Sequence
<220> FEATURE:
<223> OTHER INFORMATION: Cas12j

<400> SEQUENCE: 4

Met Pro Ser Tyr Lys Ser Ser Arg Val Leu Val Arg Asp Val Pro Glu
1               5                10                15

Glu Leu Val Asp His Tyr Glu Arg Ser His Arg Val Ala Ala Phe Phe
            20                25                30

Met Arg Leu Leu Leu Ala Met Arg Arg Glu Pro Tyr Ser Leu Arg Met
            35                40                45

Arg Asp Gly Thr Glu Arg Glu Val Asp Leu Asp Glu Thr Asp Asp Phe
        50                55                60

Leu Arg Ser Ala Gly Cys Glu Glu Pro Asp Ala Val Ser Asp Asp Leu
65                70                75                80

Arg Ser Phe Ala Leu Ala Val Leu His Gln Asp Asn Pro Lys Lys Arg
                85                90                95

Ala Phe Leu Glu Ser Glu Asn Cys Val Ser Ile Leu Cys Leu Glu Lys
            100               105               110

Ser Ala Ser Gly Thr Arg Tyr Tyr Lys Arg Pro Gly Tyr Gln Leu Leu
```

-continued

```
            115                 120                 125

Lys Lys Ala Ile Glu Glu Glu Trp Gly Trp Asp Lys Phe Glu Ala Ser
    130                 135                 140

Leu Leu Asp Glu Arg Thr Gly Glu Val Ala Glu Lys Phe Ala Ala Leu
145                 150                 155                 160

Ser Met Glu Asp Trp Arg Arg Phe Phe Ala Ala Arg Asp Pro Asp Asp
                165                 170                 175

Leu Gly Arg Glu Leu Leu Lys Thr Asp Thr Arg Glu Gly Met Ala Ala
                180                 185                 190

Ala Leu Arg Leu Arg Glu Arg Gly Val Phe Pro Val Ser Val Pro Glu
                195                 200                 205

His Leu Asp Leu Asp Ser Leu Lys Ala Ala Met Ala Ser Ala Ala Glu
    210                 215                 220

Arg Leu Lys Ser Trp Leu Ala Cys Asn Gln Arg Ala Val Asp Glu Lys
225                 230                 235                 240

Ser Glu Leu Arg Lys Arg Phe Glu Glu Ala Leu Asp Gly Val Asp Pro
                245                 250                 255

Glu Lys Tyr Ala Leu Phe Glu Lys Phe Ala Ala Glu Leu Gln Gln Ala
                260                 265                 270

Asp Tyr Asn Val Thr Lys Lys Leu Val Leu Ala Val Ser Ala Lys Phe
                275                 280                 285

Pro Ala Thr Glu Pro Ser Glu Phe Lys Arg Gly Val Glu Ile Leu Lys
    290                 295                 300

Glu Asp Gly Tyr Lys Pro Leu Trp Glu Asp Phe Arg Glu Leu Gly Phe
305                 310                 315                 320

Val Tyr Leu Ala Glu Arg Lys Trp Glu Arg Arg Gly Gly Ala Ala
                325                 330                 335

Val Thr Leu Cys Asp Ala Asp Asp Ser Pro Ile Lys Val Arg Phe Gly
                340                 345                 350

Leu Thr Gly Arg Gly Arg Lys Phe Val Leu Ser Ala Ala Gly Ser Arg
                355                 360                 365

Phe Leu Ile Thr Val Lys Leu Pro Cys Gly Asp Val Gly Leu Thr Ala
    370                 375                 380

Val Pro Ser Arg Tyr Phe Trp Asn Pro Ser Val Gly Arg Thr Thr Ser
385                 390                 395                 400

Asn Ser Phe Arg Ile Glu Phe Thr Lys Arg Thr Thr Glu Asn Arg Arg
                405                 410                 415

Tyr Val Gly Glu Val Lys Glu Ile Gly Leu Val Arg Gln Arg Gly Arg
                420                 425                 430

Tyr Tyr Phe Phe Ile Asp Tyr Asn Phe Asp Pro Glu Glu Val Ser Asp
                435                 440                 445

Glu Thr Lys Val Gly Arg Ala Phe Phe Arg Ala Pro Leu Asn Glu Ser
    450                 455                 460

Arg Pro Lys Pro Lys Asp Lys Leu Thr Val Met Gly Ile Asp Leu Gly
465                 470                 475                 480

Ile Asn Pro Ala Phe Ala Phe Ala Val Cys Thr Leu Gly Glu Cys Gln
                485                 490                 495

Asp Gly Ile Arg Ser Pro Val Ala Lys Met Glu Asp Val Ser Phe Asp
                500                 505                 510

Ser Thr Gly Leu Arg Gly Gly Ile Gly Ser Gln Lys Leu His Arg Glu
                515                 520                 525

Met His Asn Leu Ser Asp Arg Cys Phe Tyr Gly Ala Arg Tyr Ile Arg
    530                 535                 540
```

-continued

```
Leu Ser Lys Lys Leu Arg Asp Arg Gly Ala Leu Asn Asp Ile Glu Ala
545                 550                 555                 560

Arg Leu Leu Glu Glu Lys Tyr Ile Pro Gly Phe Arg Ile Val His Ile
                565                 570                 575

Glu Asp Ala Asp Glu Arg Arg Arg Thr Val Gly Arg Thr Val Lys Glu
                580                 585                 590

Ile Lys Gln Glu Tyr Lys Arg Ile Arg His Gln Phe Tyr Leu Arg Tyr
                595                 600                 605

His Thr Ser Lys Arg Asp Arg Thr Glu Leu Ile Ser Ala Glu Tyr Phe
        610                 615                 620

Arg Met Leu Phe Leu Val Lys Asn Leu Arg Asn Leu Leu Lys Ser Trp
625                 630                 635                 640

Asn Arg Tyr His Trp Thr Thr Gly Asp Arg Glu Arg Arg Gly Gly Asn
                645                 650                 655

Pro Asp Glu Leu Lys Ser Tyr Val Arg Tyr Tyr Asn Asn Leu Arg Met
                660                 665                 670

Asp Thr Leu Lys Lys Leu Thr Cys Ala Ile Val Arg Thr Ala Lys Glu
                675                 680                 685

His Gly Ala Thr Leu Val Ala Met Glu Asn Ile Gln Arg Val Asp Arg
        690                 695                 700

Asp Asp Glu Val Lys Arg Arg Lys Glu Asn Ser Leu Leu Ser Leu Trp
705                 710                 715                 720

Ala Pro Gly Met Val Leu Glu Arg Val Glu Gln Glu Leu Lys Asn Glu
                725                 730                 735

Gly Ile Leu Ala Trp Glu Val Asp Pro Arg His Thr Ser Gln Thr Ser
                740                 745                 750

Cys Ile Thr Asp Glu Phe Gly Tyr Arg Ser Leu Val Ala Lys Asp Thr
                755                 760                 765

Phe Tyr Phe Glu Gln Asp Arg Lys Ile His Arg Ile Asp Ala Asp Val
        770                 775                 780

Asn Ala Ala Ile Asn Ile Ala Arg Arg Phe Leu Thr Arg Tyr Arg Ser
785                 790                 795                 800

Leu Thr Gln Leu Trp Ala Ser Leu Leu Asp Asp Gly Arg Tyr Leu Val
                805                 810                 815

Asn Val Thr Arg Gln His Glu Arg Ala Tyr Leu Glu Leu Gln Thr Gly
                820                 825                 830

Ala Pro Ala Ala Thr Leu Asn Pro Thr Ala Glu Ala Ser Tyr Glu Leu
                835                 840                 845

Val Gly Leu Ser Pro Glu Glu Glu Leu Ala Gln Thr Arg Ile Lys
        850                 855                 860

Arg Lys Lys Arg Glu Pro Phe Tyr Arg His Glu Gly Val Trp Leu Thr
865                 870                 875                 880

Arg Glu Lys His Arg Glu Gln Val His Glu Leu Arg Asn Gln Val Leu
                885                 890                 895

Ala Leu Gly Asn Ala Lys Ile Pro Glu Ile Arg Thr
                900                 905
```

<210> SEQ ID NO 5
<211> LENGTH: 50
<212> TYPE: DNA
<213> ORGANISM: Artificial Sequence
<220> FEATURE:
<223> OTHER INFORMATION: Cas12i3-g2-ssDNA0

<400> SEQUENCE: 5

-continued gatcgttggt agttcatgct gctgtcggtg aaataaacat ctccggtaac          50

<210> SEQ ID NO 6
<211> LENGTH: 50
<212> TYPE: DNA
<213> ORGANISM: Artificial Sequence
<220> FEATURE:
<223> OTHER INFORMATION: Cas12j19-g3-ssDNA0

<400> SEQUENCE: 6
ccccgccttt tggaccaact cgcatcaatc ccatgtaggc gtcggcgatg          50

<210> SEQ ID NO 7
<211> LENGTH: 41
<212> TYPE: RNA
<213> ORGANISM: Artificial Sequence
<220> FEATURE:
<223> OTHER INFORMATION: LbCas12a-TGW6-g1

<400> SEQUENCE: 7
uaauuucuac uaaguguaga uuuucaccga cagcagcaug a          41

<210> SEQ ID NO 8
<211> LENGTH: 105
<212> TYPE: RNA
<213> ORGANISM: Artificial Sequence
<220> FEATURE:
<223> OTHER INFORMATION: AaCas12b-TGW6-g1

<400> SEQUENCE: 8
gucuaaagga cagaauuuuu caacgggugu gccaauggcc acuuuccagg uggcaaagcc          60
cguugaacuu caagcgaagu ggcacuuuca ccgacagcag cauga          105

<210> SEQ ID NO 9
<211> LENGTH: 46
<212> TYPE: RNA
<213> ORGANISM: Artificial Sequence
<220> FEATURE:
<223> OTHER INFORMATION: Cas12i3-TGW6-g2

<400> SEQUENCE: 9
agagaaugug ugcauaguca cacuuucacc gacagcagca ugaacu          46

<210> SEQ ID NO 10
<211> LENGTH: 60
<212> TYPE: RNA
<213> ORGANISM: Artificial Sequence
<220> FEATURE:
<223> OTHER INFORMATION: Cas12j19-TGW6-g3

<400> SEQUENCE: 10
gugcugcugu cucccagacg ggaggcagaa cugcacggau ugaugcgagu ugguccaaaa          60

<210> SEQ ID NO 11
<211> LENGTH: 43
<212> TYPE: RNA
<213> ORGANISM: Artificial Sequence
<220> FEATURE:
<223> OTHER INFORMATION: gRNA sequence for Cas12i

<400> SEQUENCE: 11
agagaaugug ugcauaguca cacucaggau guuaacugca cag          43

<210> SEQ ID NO 12

-continued

```
<211> LENGTH: 56
<212> TYPE: RNA
<213> ORGANISM: Artificial Sequence
<220> FEATURE:
<223> OTHER INFORMATION: gRNA sequence for Cas12j

<400> SEQUENCE: 12
gugcugcugu cucccagacg ggaggcagaa cugcaccgcg acauuccgaa gaacgc          56

<210> SEQ ID NO 13
<211> LENGTH: 40
<212> TYPE: DNA
<213> ORGANISM: Artificial Sequence
<220> FEATURE:
<223> OTHER INFORMATION: target nucleic acid EV71 VP1

<400> SEQUENCE: 13
gtgcacgcaa caaaagtgaa ctctgcatca aagcgcatgt                            40

<210> SEQ ID NO 14
<211> LENGTH: 44
<212> TYPE: RNA
<213> ORGANISM: Artificial Sequence
<220> FEATURE:
<223> OTHER INFORMATION: gRNA LbCas12a-g71-1
<220> FEATURE:
<221> NAME/KEY: misc_feature
<222> LOCATION: (1)..(21)
<223> OTHER INFORMATION: position for the gRNA to bind to the protein
<220> FEATURE:
<221> NAME/KEY: misc_feature
<222> LOCATION: (22)..(44)
<223> OTHER INFORMATION: position matching the target nucleic acid
       sequence

<400> SEQUENCE: 14
uaauuucuac uaaguguaga uaugcagagu ucacuuuugu ugcg                       44

<210> SEQ ID NO 15
<211> LENGTH: 50
<212> TYPE: DNA
<213> ORGANISM: Artificial Sequence
<220> FEATURE:
<223> OTHER INFORMATION: target nucleic acid OsTGW6

<400> SEQUENCE: 15
gatcgttggt agttcatgct gctgtcggtg aaataaacat ctccggtaac                 50

<210> SEQ ID NO 16
<211> LENGTH: 101
<212> TYPE: RNA
<213> ORGANISM: Artificial Sequence
<220> FEATURE:
<223> OTHER INFORMATION: tracrRNA sequence for Cas12b

<400> SEQUENCE: 16
gucuaaagga cagaauuuuu caacgggugu gccaauggcc acuuuccagg uggcaaagcc       60
cguugaacuu cucaaaaaga acgcucgcuc aguguucuga c                          101

<210> SEQ ID NO 17
<211> LENGTH: 56
<212> TYPE: RNA
<213> ORGANISM: Artificial Sequence
<220> FEATURE:
<223> OTHER INFORMATION: crRNA sequence for Cas12b
<220> FEATURE:
<221> NAME/KEY: misc_feature
<222> LOCATION: (37)..(56)
```

-continued

```
<223> OTHER INFORMATION: position matching the target nucleic acid
      sequence

<400> SEQUENCE: 17
gucggaucac ugagcgagcg aucugagaag uggcacuuuc accgacagca gcauga            56

<210> SEQ ID NO 18
<211> LENGTH: 59
<212> TYPE: DNA
<213> ORGANISM: Artificial Sequence
<220> FEATURE:
<223> OTHER INFORMATION: target nucleic acid COVID-19 orf1ab

<400> SEQUENCE: 18
ggcaccaaat tccaaaggtt taccttggta atcatcttca gtaccatact catattgag       59

<210> SEQ ID NO 19
<211> LENGTH: 47
<212> TYPE: RNA
<213> ORGANISM: Artificial Sequence
<220> FEATURE:
<223> OTHER INFORMATION: gRNA CV19-Lamb-i3g5g
<220> FEATURE:
<221> NAME/KEY: misc_feature
<222> LOCATION: (1)..(23)
<223> OTHER INFORMATION: position for the gRNA to bind to the protein
<220> FEATURE:
<221> NAME/KEY: misc_feature
<222> LOCATION: (24)..(47)
<223> OTHER INFORMATION: position matching the target nucleic acid
      sequence

<400> SEQUENCE: 19
agagaaugug ugcauaguca cacccaaggu aaaccuuugg aauuugg                     47
```

METHOD FOR MULTIPLEX NUCLEIC ACID DETECTION BASED ON CLUSTERED REGULARLY INTERSPACED SHORT PALINDROMIC REPEAT

CROSS REFERENCE TO THE RELATED APPLICATIONS

This is a continuation application of the national phase entry of International Application No. PCT/CN2021/114374, filed on Aug. 24, 2021, which is based upon and claims priority to Chinese Patent Application No. 202010888036.3, filed on Aug. 28, 2020; No. 202110236947.2, filed on Mar. 3, 2021; the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBSDSF003-PKG_SL.txt, created on Jan. 4, 2022, and is 41,228 bytes in size.

TECHNICAL FIELD

The present disclosure relates to the field of nucleic acid detection, relates to a method for multiplex nucleic acid detection based on clustered regularly interspaced short palindromic repeat (CRISPR), specifically to a method, system, and kit for target nucleic acid detection based on CRISPR, and more specifically to a method for multiplex target nucleic acid detection based on CRISPR.

BACKGROUND

Specific nucleic acid detection methods have important application values, such as pathogen detection and genetic disease detection. In terms of pathogen detection, since each pathogen microorganism has a unique characteristic nucleic acid sequence, it is possible to develop nucleic acid detection for a specific species, also known as nucleic acid diagnostics (NADs), which is of important significance in the fields of food safety, environmental microbial contamination detection, human pathogenic infection, and the like. In addition, the detection of single nucleotide polymorphisms (SNPs) in humans or other species is involved. The interpretation of a relationship between genetic variation and biological function at the genomic level provides a new perspective for modern molecular biology. SNPs are closely related to biological functions, evolution, and diseases. Therefore, it is particularly important to develop SNP detection and analysis techniques.

Specific nucleic acid detection methods currently established usually include two steps: 1. amplification of a target nucleic acid; and 2. detection of the target nucleic acid. Existing detection techniques include restriction endonuclease-based technique, Southern, Northern, dot-blot hybridization, fluorescent polymerase chain reaction (PCR) detection, loop-mediated isothermal amplification (LAMP), recombinase polymerase amplification (RPA), and the like. CRISPR gene editing technologies emerged after 2012. On the basis of RPA, Zhang Feng's team developed a new nucleic acid diagnostics technology (SHERLOCK technology) that takes Cas13 as core and targets RNA. Doudna's team developed a diagnostics technology (DETECTR technology) with Cas12 enzyme as core. Dr. Wang Jin et al., from Shanghai Institute of Plant Physiology and Ecology, Chinese Academy of Sciences, also developed a new nucleic acid detection technology (HOLMES technology) based on Cas12. Nucleic acid detection technologies developed based on CRISPR are playing an increasingly important role.

Although there are many nucleic acid detection technologies at present, how to achieve a rapid, simple, cheap, and accurate detection is still an important direction for improving the detection technology. In particular, how to conduct a multiplex detection on nucleic acids is an urgent problem to be solved.

SUMMARY

The present disclosure provides a method for nucleic acid detection based on CRISPR, especially a method, system, and kit for multiplex detection of a nucleic acid.

In an aspect, the present disclosure provides a method for detecting a target nucleic acid in a sample, including: contacting the sample with a nucleic acid detection composition, where the nucleic acid detection composition includes a CRISPR-associated (Cas) protein, a guide RNA (gRNA), and a single-stranded nucleic acid reporter, and the gRNA includes a region to bind to the Cas protein and a guide sequence to hybridize with a target sequence on the target nucleic acid; and detecting a detectable signal generated due to cleavage of the Cas protein on the single-stranded nucleic acid reporter to detect the target nucleic acid;

where the nucleic acid detection composition includes any one, any two, any three, or four from the group consisting of a first nucleic acid detection composition, a second nucleic acid detection composition, a third nucleic acid detection composition, and a fourth nucleic acid detection composition;

the first nucleic acid detection composition includes Cas12i, a first gRNA capable of binding to Cas12i and hybridizing with a first target sequence on the target nucleic acid, and a first single-stranded nucleic acid reporter;

the second nucleic acid detection composition includes Cas12b, a second gRNA capable of binding to Cas12b and hybridizing with a second target sequence on the target nucleic acid, and a second single-stranded nucleic acid reporter;

the third nucleic acid detection composition includes Cas12a, a third gRNA capable of binding to Cas12a and hybridizing with a third target sequence on the target nucleic acid, and a third single-stranded nucleic acid reporter; and the fourth nucleic acid detection composition includes Cas12j, a fourth gRNA capable of binding to Cas12j and hybridizing with a fourth target sequence on the target nucleic acid, and a fourth single-stranded nucleic acid reporter.

The first single-stranded nucleic acid reporter may include at least two consecutive nucleotides, and the nucleotides may be one or more from the group consisting of ribonucleotides, deoxyribonucleotides, and nucleic acid analogues; bases of the ribonucleotides may be one or more from the group consisting of A, U, C, G, T, and I; and bases of the deoxyribonucleotides may be one or more from the group consisting of A, T, C, G, U, and I.

Preferably, a nucleic acid of the first single-stranded nucleic acid reporter may include two consecutive nucleotides, and the nucleotides may be one or more from the group consisting of ribonucleotides, deoxyribonucleotides, and nucleic acid analogues.

The nucleic acid analogue may include a 2'-fluoro-modified nucleic acid, 2'-o-methyl-modified nucleic acid, a locked nucleic acid (LNA), a bridged nucleic acid (BNA), a morpholino, a glycol nucleic acid (GNA), a hexitol nucleic acid (HNA), a threose nucleic acid (TNA), arabinose nucleic acid (ANA), a 2'-methoxyacetyl-modified nucleic acid a 2'-amino-modified nucleic acid, a 4'-thio RNA, and a combination thereof; and preferably, the nucleic acid analogue may be a 2'-fluoro-modified nucleic acid.

Further, the bases of the ribonucleotides may be one or more from the group consisting of A, U, C, G, T, and I; and the bases of the deoxyribonucleotides may be one or more from the group consisting of A, T, C, G, U, and I. A base of the nucleic acid analogue may be one or more from the group consisting of A, U, C, G, T, and I; and preferably, the base of the nucleic acid analogue may be selected from the group consisting of T and/or C.

Preferably, the nucleic acid of the first single-stranded nucleic acid reporter may include two consecutive deoxynucleotides, and a base sequence of the deoxyribonucleotides may be TT or CT.

Preferably, the first single-stranded nucleic acid reporter may include two consecutive nucleic acid analogues.

More preferably, the first single-stranded nucleic acid reporter may include two consecutive 2'-fluoro-modified nucleic acid.

Further, the first single-stranded nucleic acid reporter may include two consecutive 2'-fluoro-modified T, or may be a single strand composed of 2'-fluoro-modified T and 2'-fluoro-modified C.

The second single-stranded nucleic acid reporter may be a single-stranded nucleic acid reporter with abasic spacer; or, a nucleic acid structure of the second single-stranded nucleic acid reporter may be a nucleic acid analogue, and the nucleic acid analogue is an LNA. The single-stranded nucleic acid reporter with LNA is also described in Chinese Application CN2020105609327. A base of the LNA may be one or more from the group consisting of A, T, C, G, U, and I.

The single-stranded nucleic acid reporter with abasic spacer may include at least one optional nucleotide and at least one abasic spacer; preferably, at least one abasic spacer may be linked to each of two terminals of the nucleotide; more preferably, at least two abasic spacers may be linked to each of the two terminals of the nucleotide; and in a preferred embodiment, the single-stranded nucleic acid reporter may only include one optional nucleotide.

In an embodiment, the single-stranded nucleic acid reporter with abasic spacer may include at least two non-consecutive optional nucleotides, and at least one abasic spacer may be linked between the non-consecutive optional nucleotides. In an embodiment, 2 to 20 abasic spacers may be linked between the non-consecutive optional nucleotides, preferably 2, 3, 4, 5, 6, 7, 8, 9, 10, 15, or 20 abasic spacers.

In an embodiment, 2 to 20 abasic spacers may be linked to each of two terminals of the nucleotides, preferably 2, 3, 4, 5, 6, 7, 8, 9, 10, 15, or 20 abasic spacers.

In the most preferred embodiment, the single-stranded nucleic acid reporter with an abasic spacer may include one optional nucleotide, and two abasic spacers may be linked to each of two terminals of the nucleotide.

The abasic spacer may be one or more from the group consisting of dSpacer, Spacer C3, Spacer C6, Spacer C12, Spacer9, Spacer12, Spacer18, Inverted Abasic Site (dSpacer abasic furan), and rAbasic Site (rSpacer abasic furan); and preferably, the abasic spacer may be dSpacer (abasic furan).

In the present disclosure, "dSpacer" may also be called abasic site, tetrahydrofuran (TIF) or apurinic/apyrimidinic (AP) site, or abasic linker, in which methylene is located at position 1 of 2'-deoxyribose.

dSpacer is an abasic spacer well known in the art. For example, dSpacer is disclosed in U.S. Pat. No. 8,153,772B2. dSpacer not only has a structure very similar to that of a natural site, but also is quite stable. The structure is as follows:

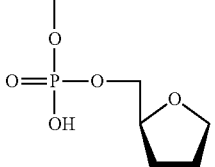

When linked to nucleotides, the dSpacer can form the following structure:

Preferably, the nucleotides may be ribonucleotides and/or deoxyribonucleotides; bases of the ribonucleotides may be one or more from the group consisting of A, U, C, G, T, and I; and bases of the deoxyribonucleotides may be one or more from the group consisting of A, T, C, G, I, and U.

Further, the nucleotides may be deoxyribonucleotides; and bases of the deoxyribonucleotides may be one or more from the group consisting of A, T, and G.

The third single-stranded nucleic acid reporter may be a single-stranded nucleic acid reporter with abasic spacer; the single-stranded nucleic acid reporter with abasic spacer may include at least one optional nucleotide and at least one abasic spacer; preferably, at least one abasic spacer may be linked to each of two terminals of the nucleotide, and more preferably, at least two abasic spacers may be linked to each of the two terminals of the nucleotide; and in a preferred embodiment, the single-stranded nucleic acid reporter may only include one optional nucleotide.

In an embodiment, 2 to 20 abasic spacers may be linked to each of two terminals of the nucleotide, preferably 2, 3, 4, 5, 6, 7, 8, 9, 10, 15, or 20 abasic spacers.

In the most preferred embodiment, the single-stranded nucleic acid reporter with abasic spacer may include one optional nucleotide, and two abasic spacers may be linked to each of two terminals of the nucleotide.

The abasic spacer may be dSpacer (abasic furan).

Preferably, the nucleotide may be a ribonucleotide and/or a deoxyribonucleotide; a base of the ribonucleotide may be one or more from the group consisting of A, U, C, G, T, and I; and a base of the deoxyribonucleotide may be one or more from the group consisting of A, T, C, G, I, and U.

The fourth single-stranded nucleic acid reporter may be a single-stranded nucleic acid reporter with abasic spacer; or, a nucleic acid structure of the fourth single-stranded nucleic acid reporter may be a nucleic acid analogue, the nucleic acid analogue may be 2'-O-methyl RNA, and a base of the 2'-O-methyl RNA may be one or more from the group consisting of A, T, U, C, G, and I.

The single-stranded nucleic acid reporter with abasic spacer may include at least one optional nucleotide and at least one abasic spacer; preferably, at least one abasic spacer may be linked to each of two terminals of the nucleotide; more preferably, at least two abasic spacers may be linked to each of the two terminals of the nucleotide; and in a preferred embodiment, the single-stranded nucleic acid reporter may only include one optional nucleotide.

In an embodiment, 2 to 20 abasic spacers may be linked to each of two terminals of the nucleotide, preferably 2, 3, 4, 5, 6, 7, 8, 9, 10, 15, or 20 abasic spacers.

In the most preferred embodiment, the single-stranded nucleic acid reporter with an abasic spacer may include one optional nucleotide, and two abasic spacers may be linked to each of two terminals of the nucleotide.

The abasic spacer may be dSpacer (abasic furan).

The nucleotide may be a ribonucleotide and/or a deoxyribonucleotide; a base of the ribonucleotide may be one or more from the group consisting of A, U, C, G, T, and I; and a base of the deoxyribonucleotide may be one or more from the group consisting of A, T, C, G, I, and U.

Further, the nucleotide may be a deoxyribonucleotide; and a base of the deoxyribonucleotide may be T.

In the present disclosure, compared with other Cas proteins, the Cas12i can specifically cleave the first single-stranded nucleic acid reporter, thereby generating a first detectable signal; compared with other Cas proteins, the Cas12b can specifically cleave the second single-stranded nucleic acid reporter, thereby generating a second detectable signal; compared with other Cas proteins, the Cas12a can specifically cleave the third single-stranded nucleic acid reporter, thereby generating a third detectable signal; and compared with other Cas proteins, the Cas12j can specifically cleave the fourth single-stranded nucleic acid reporter, thereby generating a fourth detectable signal.

The above-mentioned specific cleavage means that, compared with other proteins, a given protein shows a higher cleavage efficiency and leads to a better detectable signal for a single-stranded nucleic acid reporter targeted by the protein.

The detectable signal may be detected in the following ways: visual-based detection, sensor-based detection, color detection, gold nanoparticle-based detection, fluorescence polarization, fluorescent signal-based detection, colloidal phase transition/dispersion, electrochemical detection, and semiconductor-based detection.

In the present disclosure, the detectable signal may be any signal generated when the single-stranded nucleic acid reporter is cleaved. For example, gold nanoparticle-based detection, fluorescence polarization, fluorescent signal-based detection, colloidal phase transition/dispersion, electrochemical detection, and semiconductor-based sensing all are possible. The detectable signal can be read out in any suitable way, including but not limited to: measurement of a detectable fluorescent signal, gel electrophoresis detection (by detecting a change of a band on a gel), determination of a color based on vision or a sensor, or determination of difference in color (for example, based on gold nanoparticles) and difference in electrical signal.

In a preferred embodiment, the first detectable signal, the second detectable signal, the third detectable signal, and the fourth detectable signal may be different from each other.

Preferably, two terminals of the single-stranded nucleic acid reporter may be provided with a fluorophore and a quencher respectively; and when the single-stranded nucleic acid reporter is cleaved, a detectable fluorescent signal can be presented. The fluorophore may be one or more from the group consisting of FAM, FITC, VIC, JOE, TET, CY3, CY5, ROX, Texas Red, and LC RED460; and the quencher may be one or more from the group consisting of BHQ1, BHQ2, BHQ3, Dabcyl, and Tamra.

In an embodiment, the two terminals of the first single-stranded nucleic acid reporter may be provided with a first fluorophore and a first quencher respectively, the two terminals of the second single-stranded nucleic acid reporter may be provided with a second fluorophore and a second quencher respectively, the two terminals of the third single-stranded nucleic acid reporter may be provided with a third fluorophore and a third quencher respectively, and the two terminals of the fourth single-stranded nucleic acid reporter may be provided with a fourth fluorophore and a fourth quencher respectively; the first fluorophore, the second fluorophore, the third fluorophore, and the fourth fluorophore may be the same or different from each other; and the first quencher, the second quencher, the third quencher, and the fourth quencher may be the same or different from each other.

In other embodiments, a 5' terminus and a 3' terminus of the single-stranded nucleic acid reporter may be provided with different labeling molecules respectively. The single-stranded nucleic acid reporter is subjected to a colloidal gold test before and after being cleaved by the Cas protein; and the single-stranded nucleic acid reporter shows different chromogenic results on the colloidal gold detection line and control line before and after being cleaved by the Cas protein.

In the present disclosure, the first target sequence, the second target sequence, the third target sequence, and the fourth target sequence may be the same or different from each other.

According to actual needs, those skilled in the art can determine the first target sequence, the second target sequence, the third target sequence, and the fourth target sequence to be the same, or different, or partly the same.

Preferably, the above-mentioned target sequences may be different from each other, such that the method for detecting a target nucleic acid of the present disclosure can realize the multiplex detection of a nucleic acid in a sample. In an embodiment, the first target sequence, the second target sequence, the third target sequence, and the fourth target sequence may be target sequences designed for the same target nucleic acid or different sites of the same gene, or target sequences designed for different target nucleic acids or different genes. In an embodiment, different target sequences can be designed for a bacterium, virus, or disease-related nucleic acid. In other embodiments, different target sequences can be designed for different bacterium, virus, or disease-related nucleic acids.

In an embodiment, a combination of the first nucleic acid detection composition with the second nucleic acid detection composition, the third nucleic acid detection composition, or the fourth nucleic acid detection composition can be used to achieve the doublet detection of a target nucleic acid.

In another embodiment, a combination of the second nucleic acid detection composition with the third nucleic acid detection composition or the fourth nucleic acid detection composition can be used to achieve the doublet detection of a target nucleic acid. In such an embodiment, a nucleic acid structure of the second single-stranded nucleic acid reporter in the second nucleic acid detection composition may be a nucleic acid analogue, and the nucleic acid analogue may be an LNA.

In another embodiment, a combination of the second nucleic acid detection composition with the fourth nucleic acid detection composition can be used to achieve the doublet detection of a target nucleic acid. In such an embodiment, the second single-stranded nucleic acid reporter in the second nucleic acid detection composition may be a single-stranded nucleic acid reporter with an abasic spacer; preferably, a base of a nucleotide in the second single-stranded nucleic acid reporter in the second nucleic acid detection composition may be one or more from the group consisting of A, T, and G; a nucleic acid structure of the fourth single-stranded nucleic acid reporter may be a nucleic acid analogue, and the nucleic acid analogue may be 2'-O-methyl RNA; and preferably, a base of the 2'-O-methyl RNA may be one or more from the group consisting of A, T, U, C, G, and I.

In another embodiment, a combination of the third nucleic acid detection composition with the fourth nucleic acid detection composition can be used to achieve the doublet detection of a target nucleic acid. In such an embodiment, the third single-stranded nucleic acid reporter in the third nucleic acid detection composition may be a single-stranded nucleic acid reporter with an abasic spacer; a nucleic acid structure of the fourth single-stranded nucleic acid reporter may be a nucleic acid analogue, and the nucleic acid analogue may be 2'-O-methyl RNA; and preferably, a base of the 2'-O-methyl RNA may be one or more from the group consisting of A, T, U, C, G, and I.

In another embodiment, a combination of the first nucleic acid detection composition and the second nucleic acid detection composition with any one selected from the group consisting of the third nucleic acid detection composition and the fourth nucleic acid detection composition can be used to achieve the triplet detection of a target nucleic acid. In such an embodiment, a nucleic acid structure of the second single-stranded nucleic acid reporter in the second nucleic acid detection composition may be a nucleic acid analogue, and the nucleic acid analogue may be an LNA.

In another embodiment, a combination of the third nucleic acid detection composition and the fourth nucleic acid detection composition with any one selected from the group consisting of the first nucleic acid detection composition and the second nucleic acid detection composition can be used to achieve the triplet detection of a target nucleic acid. In such an embodiment, a nucleic acid structure of the second single-stranded nucleic acid reporter in the second nucleic acid detection composition may be a nucleic acid analogue, and the nucleic acid analogue may be an LNA; a base of a nucleotide in the third single-stranded nucleic acid reporter in the third nucleic acid detection composition may be C; a nucleic acid structure of the fourth single-stranded nucleic acid reporter may be a nucleic acid analogue, and the nucleic acid analogue may be 2'-O-methyl RNA; and a base of the 2'-O-methyl RNA may be one or more from the group consisting of A, T, U, C, G, and I.

In other embodiments, a combination of the first nucleic acid detection composition, the second nucleic acid detection composition, the third nucleic acid detection composition, and the fourth nucleic acid detection composition can be used to achieve the quartet detection of a target nucleic acid. In such an embodiment, a nucleic acid structure of the second single-stranded nucleic acid reporter in the second nucleic acid detection composition may be a nucleic acid analogue, and the nucleic acid analogue may be an LNA. In such an embodiment, a base of a nucleotide in the third single-stranded nucleic acid reporter in the third nucleic acid detection composition may be C; a nucleic acid structure of the fourth single-stranded nucleic acid reporter may be a nucleic acid analogue, and the nucleic acid analogue may be 2'-O-methyl RNA; and a base of the 2'-O-methyl RNA may be one or more from the group consisting of A, T, U, C, G, and I.

For example, when the first nucleic acid detection composition and the second nucleic acid detection composition are used for doublet detection, different target sequences can be designed for the virus SARS-CoV2 (COVID-19) to achieve the doublet detection of two target nucleic acids of SARS-CoV2 (COVID-19); or, a first target sequence and a second target sequence can be designed for the viruses SARS-CoV2 (COVID-19) and SARS respectively to achieve the doublet detection of the two viruses SARS-CoV2 (COVID-19) and SARS.

In another aspect, the present disclosure provides a method for multiplex detection of a target nucleic acid in a sample, including: contacting the sample with a nucleic acid detection composition, where the nucleic acid detection composition includes a Cas protein, a gRNA, and a single-stranded nucleic acid reporter, and the gRNA includes a region to bind to the Cas protein and a guide sequence to hybridize with a target sequence on the target nucleic acid; and detecting a detectable signal generated due to cleavage of the Cas protein on the single-stranded nucleic acid reporter to detect the target nucleic acid; where the nucleic acid detection composition includes any one, any two, any three, or four from the group consisting of the first nucleic acid detection composition, the second nucleic acid detection composition, the third nucleic acid detection composition, and the fourth nucleic acid detection composition described above.

In another aspect, the present disclosure provides a nucleic acid detection composition including any one, any two, any three, or four from the group consisting of the first nucleic acid detection composition, the second nucleic acid detection composition, the third nucleic acid detection composition, and the fourth nucleic acid detection composition described above.

In another aspect, the present disclosure also provides a system for detecting a target nucleic acid in a sample, including a nucleic acid detection composition, where the nucleic acid detection composition includes a Cas protein, a gRNA, and a single-stranded nucleic acid reporter; the gRNA includes a region to bind to the Cas protein and a guide sequence to hybridize with a target sequence on the target nucleic acid; and the nucleic acid detection composition includes any one, any two, any three, or four from the group consisting of the first nucleic acid detection composition, the second nucleic acid detection composition, the third nucleic acid detection composition, and the fourth nucleic acid detection composition described above.

In another aspect, the present disclosure also provides a kit for detecting a target nucleic acid in a sample, including a nucleic acid detection composition, where the nucleic acid detection composition includes a Cas protein, a gRNA, and a single-stranded nucleic acid reporter, and the gRNA includes a region to bind to the Cas protein and a guide sequence to hybridize with a target sequence on the target nucleic acid. The nucleic acid detection composition includes any one, any two, any three, or four from the group consisting of the first nucleic acid detection composition, the second nucleic acid detection composition, the third nucleic acid detection composition, and the fourth nucleic acid detection composition described above.

In another aspect, the present disclosure also provides use of the above-mentioned system or kit in the detection of a target nucleic acid in a sample. As described above, when the system or kit of the present disclosure is used to detect a target nucleic acid in a sample, one or more from the group consisting of the first nucleic acid detection composition, the second nucleic acid detection composition, the third nucleic acid detection composition, and the fourth nucleic acid detection composition can be used to detect the same target sequence, or detect different target sequences, thereby achieving the doublet, triplet, or quartet detection effect.

In another aspect, the present disclosure also provides use of the nucleic acid detection composition in the detection of a target nucleic acid in a sample, or use in the production of a system or kit for detecting a target nucleic acid in a sample. The nucleic acid detection composition includes any one, any two, any three, or four from the group consisting of the first nucleic acid detection composition, the second nucleic acid detection composition, the third nucleic acid detection composition, and the fourth nucleic acid detection composition described above.

In the present disclosure, the target nucleic acid may include ribonucleotides or deoxyribonucleotides; and the target nucleic acid may include a single-stranded nucleic acid and a double-stranded nucleic acid, such as single-stranded DNA, double-stranded DNA, single-stranded RNA, and double-stranded RNA.

In some embodiments, the method of the present disclosure may further include: measuring a detectable signal produced by the CRISPR/CAS effector protein (Cas protein). The Cas protein can stimulate the cleavage activity of the single-stranded nucleic acid after recognizing the target nucleic acid or hybridizing with the target nucleic acid, thereby cleaving the single-stranded nucleic acid reporter to generate a detectable signal.

In an embodiment, the target nucleic acid may be derived from a sample such as a virus, a bacterium, a microorganism, soil, a water source, a human body, an animal, and a plant. Preferably, the target nucleic acid may be a product of enrichment or amplification by a method such as PCR, NASBA, RPA, SDA, LAMP, HAD, NEAR, MDA, RCA, LCR, and RAM.

In an embodiment, the method of the present disclosure may further include: extracting the target nucleic acid from the sample.

In an embodiment, the target nucleic acid may be a viral nucleic acid, a bacterial nucleic acid, a disease-related specific nucleic acid such as a specific mutation site or a single nucleotide polymorphism (SNP) site, or a nucleic acid different from a control; preferably, the virus may be a plant virus or an animal virus, such as papilloma virus, liver DNA virus, herpes virus, adenovirus, poxvirus, parvovirus, and coronavirus; and preferably, the virus may be a coronavirus, such as SARS, SARS-CoV2 (COVID-19), HCoV-229E, HCoV-OC43, HCoV-NL63, HCoV-HKU1, and Mers-Cov.

In some embodiments, the target nucleic acid may be derived from a cell, for example, from a cell lysate.

In some embodiments, the measurement of the detectable signal may be quantitative, and in other embodiments, the measurement of the detectable signal may be qualitative.

In an embodiment, the method may further include: extracting the target nucleic acid from the sample.

In some embodiments, the target nucleic acid may be derived from a cell, for example, from a cell lysate.

In some embodiments, the measurement of the detectable signal may be quantitative, and in other embodiments, the measurement of the detectable signal may be qualitative.

In the present disclosure, the guide sequence may be of 10 bp to 40 bp, preferably 12 bp to 25 bp, preferably 15 bp to 23 bp, and preferably 16 bp to 18 bp.

In the present disclosure, the gRNA and the target sequence on the target nucleic acid may have a matching degree of at least 50%, preferably at least 60%, preferably at least 70%, preferably at least 80%, and preferably at least 90%.

In an embodiment, when the target sequence includes one or more characteristic sites (such as specific mutation sites or SNPs), the characteristic sites completely match the gRNA.

In an embodiment, the detection method may include one or more gRNAs with different guide sequences, which target different target sequences.

In an embodiment, the Cas12a may be one or more from the group consisting of FnCas12a, AsCas12a, LbCas12a, Lb5Cas12a, HkCas12a, OsCas12a, TsCas12a, BbCas12a, BoCas12a, and Lb4Cas12a; and the Cas12a may preferably be LbCas12a with an amino acid sequence shown in SEQ ID NO: 1, or a derived protein that is obtained through substitution, deletion, or addition of one or more (such as 2, 3, 4, 5, 6, 7, 8, 9, or 10) amino acid residues based on the amino acid sequence shown in SEQ ID NO: 1 or an active fragment thereof and has basically the same function as the amino acid sequence.

In other embodiments, the Cas12b may have an amino acid sequence shown in SEQ ID NO: 2, or may be a derived protein that is obtained through substitution, deletion, or addition of one or more (such as 2, 3, 4, 5, 6, 7, 8, 9, or 10) amino acid residues based on the amino acid sequence shown in SEQ ID NO: 2 or an active fragment thereof and has basically the same function as the amino acid sequence.

In other embodiments, the Cas12i may have an amino acid sequence shown in SEQ ID NO: 3, or may be a derived protein that is obtained through substitution, deletion, or addition of one or more (such as 2, 3, 4, 5, 6, 7, 8, 9, or 10) amino acid residues based on the amino acid sequence shown in SEQ ID NO: 3 or an active fragment thereof and has basically the same function as the amino acid sequence.

In other embodiments, the Cas12j may have an amino acid sequence shown in SEQ ID NO: 4, or may be a derived protein that is obtained through substitution, deletion, or addition of one or more (such as 2, 3, 4, 5, 6, 7, 8, 9, or 10) amino acid residues based on the amino acid sequence shown in SEQ ID NO: 4 or an active fragment thereof and has basically the same function as the amino acid sequence.

The term "hybridization" or "complementary" or "substantially complementary" means that a nucleic acid (such as RNA and DNA) includes a nucleotide sequence that enables its non-covalent binding, that is, the nucleic acid can form base pairs and/or G/U base pairs with another nucleic acid in a sequence-specific, anti-parallel manner (namely, the nucleic acid specifically binds to a complementary nucleic acid), "annealing" or "hybridizing". The hybridization requires that two nucleic acids include complementary sequences. There may be mismatches between bases. Suitable conditions for hybridization between two nucleic acids depend on the length and complementarity degree of the nucleic acids, which are variables well known in the art. Typically, a hybridizable nucleic acid may include 8 nucleotides or more (such as 10 nucleotides or more, 12 nucleotides or more, 15 nucleotides or more, 20 nucleotides or more, 22 nucleotides or more, 25 nucleotides or more, or 30 nucleotides or more).

It should be understood that a sequence of a polynucleotide does not need to be 100% complementary to a sequence of its target nucleic acid for specific hybridization. A polynucleotide may have 60% or more, 65% or more, 70% or more, 75% or more, 80% or more, 85% or more, 90% or more, 95% or more, 98% or more, 99% or more, 99.5% or more, or 100% complementarity with a sequence of a target region in a target nucleic acid sequence to hybridize with the polynucleotide.

General Definitions

Unless otherwise defined, the technical and scientific terms used herein have the same meanings as commonly understood by one of ordinary skill in the art.

The term "amino acid" refers to a carboxylic acid with amino. Various proteins in organisms are composed of 20 essential amino acids.

The terms "polynucleotide", "nucleotide sequence", "nucleic acid sequence", "nucleic acid molecule", and "nucleic acid" may be used interchangeably and include DNA, RNA, or a hybrid thereof, which may be double-stranded or single-stranded.

The term "oligonucleotide" refers to a sequence with 3 to 100 nucleotides, preferably 3 to 30 nucleotides, more preferably 4 to 20 nucleotides, and further more preferably 5 to 15 nucleotides.

The term "homology" or "identity" used refers to sequence matching between two polypeptides or between two nucleic acids. When given positions in two sequences to be compared are occupied by the same base or amino acid monomer subunit (for example, a given position in each of two DNA molecules is occupied by adenine, or a given position in each of two polypeptides is occupied by lysine), the molecules are the same at the position. Generally, the comparison is conducted when two sequences are aligned to produce maximum identity. The alignment can be conducted as follows: For example, the identity of amino acid sequences can be determined by a conventional method (with reference to, for example, teaching content of Smith and Waterman, 1981, Adv. Appl. Math. 2: 482 Pearson&Lipman, 1988, Proc. Natl. Acad. Sci. USA 85:2444, Thompson et al., 1994, Nucleic Acids Res 22:467380) or a computerized operating algorithm (GAP, BESTFIT, FASTA, and TFASTA in the Wisconsin Genetics software package, Genetics Computer Group). The identity can also be determined by the BLAST algorithm available from the National Center for Biotechnology Information (NCBI, www.ncbi.nlm.nih.gov/) based on default parameters.

As used herein, "CRISPR" refers to clustered regularly interspaced short palindromic repeats, which come from the immune system of microorganisms.

As used herein, "biotin" is also called vitamin H, which is a small-molecule vitamin with a molecular weight of 244

Da. "Avidin", also known as antibiotin, is a basic glycoprotein with 4 binding sites that show extremely high affinity to biotin. Streptavidin is a commonly used avidin. The extremely strong affinity of biotin to avidin can be used to amplify or enhance a detection signal in a detection system. For example, biotin easily binds to a protein (such as an antibody) through a covalent bond, and an avidin molecule binding to an enzyme reacts with a biotin molecule binding to a specific antibody, which not only plays a multi-stage amplification role, but also achieves the purpose of detecting an unknown antigen (or antibody) molecule due to a chromogenic reaction under the catalytic action of the enzyme when encountering a corresponding substrate.

Nucleic Acid Analogue

As used herein, "nucleic acid analogue" includes, but is not limited to: 2'-O-methyl (—$OCH_3$) RNA, LNA, BNA, morpholino, GNA, HNA, TNA, ANA, 2'-methoxyacetyl RNA, 2'-fluoro (—F) RNA, 2'-amino RNA, 4'-thio RNA, and a combination thereof, including optional ribonucleotide or deoxyribonucleotide residues.

LNA: LNA is a 2'-modified nucleoside, including a diradical linking the C2' and C4' of a ribose ring of the nucleoside, and the diradical restricts or locks a conformation of the ribose ring. A structural formula of LNA is shown as follows. A base of LNA can be selected from the group consisting of adenine, cytosine, guanine, 5-methyl-cytosine, thymine, and uracil.

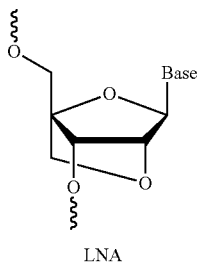

LNA

2'-O-methyl RNA (2'-O-methyl RNA, 2'-O-methyl, 2'-O-methyl-substituted RNA, and —$OCH_3$): 2'-O-methyl RNA is a 2'-modified nucleoside, in which a methoxy group (—$OCH_3$) is linked to C2' of a ribose ring of the nucleoside. A structure of a 2'-O-methyl RNA monomer is shown as follows, and a base of the 2'-O-methyl RNA can be selected from the group consisting of adenine, cytosine, guanine, 5-methyl-cytosine, thymine, and uracil.

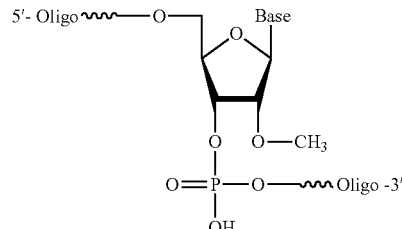

A 2'-fluoro-modified nucleic acid analogue, also known as 2'-fluoro RNA, is a 2'-modified nucleoside, in which an F (—F) is linked to C2' of a ribose ring of the nucleoside. A structure of a 2'-fluoro RNA monomer is shown as follows, and a base of the 2'-fluoro RNA can be selected from the group consisting of adenine, cytosine, guanine, 5-methyl-cytosine, thymine, and uracil.

2'F-RNA

Abasic Spacer

As used herein, "abasic spacer" refers to a nucleoside that does not include specific encoding information. An abasic spacer can be linked to an oligonucleotide, which is at a 3' or 5' terminus or within the nucleotide chain. Common Spacer includes dSpacer (abasic furan), Spacer C3, Spacer C6, Spacer C12, Spacer9, Spacer12, Spacer18, Inverted Abasic Site (dSpacer abasic furan), and rAbasic Site (rSpacer abasic furan).

The above-mentioned abasic spacers are known in the art. For example, dSpacer, Spacer 9, Spacer 18, and Spacer C3 are disclosed in U.S. Pat. No. 8,153,772B2; and dSpacer is disclosed in Chinese Patent CN101454451A.

The preferred abasic spacer "dSpacer" herein is also called abasic site, THF or apurinic/apyrimidinic (AP) site, or abasic linker, in which methylene is located at position 1 of 2'-deoxyribose. dSpacer not only has a structure very similar to that of a natural site, but also is quite stable. The structure is as follows:

When linked to nucleotides, the dSpacer can form the following structure:

5'- Oligo

Oligo -3'

Target Nucleic Acid

As used herein, the "target nucleic acid" refers to a polynucleotide molecule extracted from a biological sample (sample to be tested). The biological sample is any solid or fluid sample obtained from or excreted or secreted by any organism, including but not limited to unicellular organisms, such as bacteria, yeast, protozoa, and amoebae; and multicellular organisms (such as plants or animals, including samples from healthy or apparently healthy human subjects or human patients affected by conditions or diseases to be diagnosed or investigated, such as infection of pathogenic microorganisms such as pathogenic bacteria or viruses). For example, a biological sample can be a biological fluid obtained from, for example, blood, plasma, serum, urine, stool, sputum, mucus, lympha, synovial fluid, bile, ascitic fluid, pleural effusion, seroma, saliva, cerebrospinal fluid, aqueous or vitreous fluid, or anybody secretion and exudate (such as a fluid obtained from an abscess or any other infected or inflammatory site) or a fluid obtained from a joint (for example, a normal joint or a joint affected by a disease, such as rheumatoid arthritis (RA), osteoarthritis (OA), gout, or septic arthritis), or a swab that has been applied on the surface of skin or mucosa. The sample can also be a sample obtained from any organ or tissue (including a biopsy or autopsy specimen, such as tumor biopsy) or can include cells (primary cells or cultivated cells) or a medium conditioned by any cell, tissue, or organ. Exemplary samples include, but are not limited to, cells, cell lysates, blood smears, cell centrifugation preparations, cytologic smears, body fluids (such as blood, plasma, serum, saliva, sputum, urine, bronchoalveolar lavage, and semen), tissue biopsy specimens (such as tumor biopsy specimens), fine needle aspiration (FNA) specimens, and/or tissue sections (such as cryostat tissue sections and/or paraffin-embedded tissue sections).

In other embodiments, the biological sample may be a plant cell, a callus, a tissue, or an organ (such as root, stem, leaf, flower, seed, and fruit).

In the present disclosure, the target nucleic acid may also include a DNA molecule obtained from reverse transcription of RNA. Further, the target nucleic acid can be amplified by a technique known in the art, and the amplification technique may be an isothermal amplification technique and a non-isothermal amplification technique. The isothermal amplification can be nucleic acid sequence-based amplification (NASBA), RPA, LAMP, strand displacement amplification (SDA), helicase-dependent amplification (HDA), or nicking enzyme amplification reaction (NEAR). In some exemplary embodiments, a non-isothermal amplification technique can be adopted, including but not limited to PCR, multiple displacement amplification (MDA), rolling circle amplification (RCA), ligase chain reaction (LCR), or ramification amplification (RAM).

Further, the detection method of the present disclosure may also include: amplifying the target nucleic acid; and the detection system may also include a reagent for amplifying the target nucleic acid. The reagent for amplification includes one or more from the group consisting of DNA polymerase, strand displacement enzyme, helicase, recombinase, and single-stranded binding protein.

Cas Protein

The "Cas protein" used herein refers to a CRISPR-associated protein, preferably a type V or VI CRISPR/CAS protein. Once the Cas protein binds to a characteristic sequence (target sequence) to be detected (that is, a ternary complex of Cas protein-gRNA-target sequence is formed), its trans activity can be induced. That is, the Cas protein can randomly cleave a non-targeted single-stranded nucleotides (namely, the single-stranded nucleic acid reporter described herein). After the Cas protein binds to a characteristic sequence, its trans activity can be induced regardless of whether the characteristic sequence is cleaved or not. Preferably, the trans activity of the Cas protein may be induced by cleaving a characteristic sequence; and more preferably, the trans activity of the Cas protein may be induced by cleaving a single-stranded characteristic sequence. The Cas protein recognizes a characteristic sequence by recognizing protospacer adjacent motif (PAM) close to the characteristic sequence.

The Cas protein of the present disclosure may be a protein with at least trans-cleavage activity, and preferably, the Cas protein may be a protein with Cis and trans-cleavage activity. The Cis activity refers to the activity of the Cas protein to recognize a PAM site and specifically cleave a target sequence under the action of gRNA.

The Cas protein of the present disclosure includes type V CRISPR/CAS effector proteins, including protein families such as Cas12 and Cas14. Preferably, the Cas12 protein family may include Cas12a, Cas12b, Cas12i, and Cas12j; and preferably, the Cas14 protein family may include Cas14a, Cas14b, and the like.

In an embodiment, the Cas protein mentioned herein, such as Cas12, also encompasses a functional variant or a homologue or an orthologue of Cas. The "functional variant" of a protein as used herein refers to a variant of the protein that at least partially retains the activity of the protein. The functional variant may include a mutant (which may be an insertion, deletion, or substitution mutant), including polymorph and the like. The functional variant may also include a fusion product of such a protein with another nucleic acid, protein, polypeptide, or peptide that is normally unrelated. The functional variant may be natural or artificial. Advantageous embodiments may involve engineered or non-natural type V DNA targeting effector proteins.

In an embodiment, one or more nucleic acid molecules encoding the Cas protein such as Cas12, or an orthologue or homologue thereof can be optimized by a codon for expression in eukaryotes. The eukaryotes can be as described herein. One or more nucleic acid molecules may be engineered or non-natural.

In an embodiment, the Cas12 protein or the orthologue or homologue thereof may include one or more mutations, and thus the nucleic acid molecule encoding the protein may have one or more mutations. The mutation may be an artificially introduced mutation and may include, but is not limited to, one or more mutations in a catalytic domain.

In an embodiment, the Cas protein may come from Leptotrichia, *Listeria, Corynebacterium, Sutterella, Legionella, Treponema, Actinomyces, Eubacterium, Streptococcus, Lactobacillus, Mycoplasma, Bacteroides, Flaviivola, Flavobacterium, Azospirillum, Sphaerochaeta, Gluconacetobacter, Neisseria, Rothia, Parvibaculum, Staphylococcus, Nitratifractor, Campylobacter*, and *Lachnospira*.

In an embodiment, the Cas protein may be selected from the group consisting of the following proteins:

(1) proteins shown in SEQ ID NOS: 1-4; and (2) derived proteins that are obtained through substitution, deletion, or addition of one or more (such as 2, 3, 4, 5, 6, 7, 8, 9, or 10) amino acid residues based on the amino acid sequences shown in SEQ ID NOS: 1-4 or active fragments thereof and have basically the same function as the amino acid sequences.

In an embodiment, the Cas protein may further include a protein that has 50%, preferably 55%, preferably 60%, preferably 65%, preferably 70%, preferably 75%, preferably 80%, preferably 85%, preferably 90%, and preferably 95% sequence identity with the above sequences, and shows the trans activity.

The Cas protein can be obtained by the recombinant expression vector technology. That is, the nucleic acid molecule encoding the protein is introduced into a suitable vector, and then transformed into a host cell, such that the coding nucleic acid molecule is expressed in the cell, thereby obtaining the corresponding protein. The protein can be secreted by the cell, or the cell can be lysed through a conventional extraction technique to obtain the protein. The coding nucleic acid molecule may be integrated into a genome of the host cell for expression, or may not be integrated into the genome of the host cell for expression. The vector may further include regulatory elements that facilitate sequence integration or self-replication. The vector can be, for example, a plasmid, a virus, a cosmid, a phage, and the like, which are well known to those skilled in the art. Preferably, the expression vector in the present disclosure may be a plasmid. The vector may further include one or more regulatory elements, which are selected from the group consisting of a promoter, an enhancer, a ribosome binding site (RBS) for translation initiation, a terminator, a polyadenylic acid sequence, and a selective marker gene.

The host cell can be a prokaryote, such as *Escherichia coli* (*E. coli*), *Streptomyces*, and *Agrobacterium*; or a lower eukaryote, such as a yeast cell; or a higher eukaryote, such as a plant cell. Those of ordinary skill in the art know how to select appropriate vectors and host cells.

gRNA

As used herein, the "gRNA" is guide RNA, and has the meaning commonly understood by those skilled in the art. Generally, the gRNA can include direct repeats and guide sequences, or may be essentially composed of direct repeats and guide sequences (also called spacers in the context of endogenous CRISPR systems). In different CRISPR systems, the gRNA may include crRNA and tracrRNA, or may only include crRNA, which depends on a Cas protein that the gRNA relies on. crRNA and tracrRNA can be artificially modified and fused to form a single guide RNA (sgRNA). In some cases, the guide sequence can be any polynucleotide sequence that shows sufficient complementarity with a target sequence (the characteristic sequence in the present disclosure) to hybridize with the target sequence and guide the specific binding of the CRISPR/Cas complex to the target sequence, which usually has a sequence length of 12 nt to 25 nt. The direct repeats can be folded to form a specific structure (such as a stem-loop structure) for the Cas protein to recognize, thereby forming a complex. The guide sequence does not need to be 100% complementary to the characteristic sequence (target sequence). The guide sequence is not complementary to the single-stranded nucleic acid reporter.

In some embodiments, under optimal alignment, a complementarity (match) degree between the guide sequence and a corresponding target sequence may be at least 50%, at least 60%, at least 70%, at least 80%, at least 90%, at least 95%, or at least 99%. Determining the optimal alignment is within the competence of those of ordinary skill in the art. For example, there are published and commercially available alignment algorithms and programs, including but not limited to Smith-Waterman, Bowtie, Geneious, Biopython, and SeqMan in ClustalW and matlab.

The gRNA of the present disclosure may be natural, or may be artificially modified or designed and synthesized.

Single-Stranded Nucleic Acid Reporter

Two terminals of the single-stranded nucleic acid reporter of the present disclosure include different reporter groups or labeling molecules. When the single-stranded nucleic acid reporter is in an initial state (that is, when the single-stranded nucleic acid reporter is not cleaved), no reporter signal is presented; and when the single-stranded nucleic acid reporter is cleaved, a detectable signal is presented, indicating a detectable difference before and after cleavage. In the present disclosure, if the detectable difference can be detected, it indicates that the target nucleic acid includes the characteristic sequence to be detected; or, if the detectable difference cannot be detected, it indicates that the target nucleic acid does not include the characteristic sequence to be detected.

In an embodiment, the reporter groups or labeling molecules may include fluorophores and quenchers. The fluorophores may be one or more from the group consisting of FAM, FITC, VIC, JOE, TET, CY3, CY5, ROX, Texas Red, and LC RED460; and the quenchers may be one or more from the group consisting of BHQ1, BHQ2, BHQ3, Dabcyl, and Tamra.

In an embodiment, the single-stranded nucleic acid reporter may have a first molecule (such as FAM or FITC) linked to the 5' terminus and a second molecule (such as biotin) linked to the 3' terminus. The reaction system with a single-stranded nucleic acid reporter may be used in combination with a flow strip to detect a characteristic sequence (preferably, colloidal gold detection). The flow strip is designed to have two capture lines, where an antibody to bind to a first molecule (namely, an anti-first molecule antibody) is arranged at a sample contact end (colloidal gold), an antibody to bind to the anti-first molecule antibody is arranged at a first line (control line), and an antibody to bind to a second molecule (namely, an anti-second molecule antibody, such as avidin) is arranged at a second line (test line). As a reaction proceeds along the strip, the anti-first molecule antibody binds to the first molecule and carries a cleaved or uncleaved oligonucleotide to the capture line, where a cleaved reporter will bind to the antibody binding to the anti-first molecule antibody at the first capture line; and an uncleaved reporter will bind to the anti-second molecule antibody at the second capture line. The binding of the reporter group to each line will result in a strong readout/ signal (such as color). As more reporters are cut, more signals will accumulate at the first capture line, and fewer signals will appear at the second line. In some aspects, the present disclosure relates to use of the flow strip as described herein in the detection of a nucleic acid. In some aspects, the present disclosure relates to a method for detecting a nucleic acid using a flow strip as defined herein, such as a (lateral) flow test or a (lateral) flow immunochromatographic assay. In some aspects, the molecules in the single-stranded nucleic acid reporter can be used instead of each other, or positions of the molecules can be changed. As long as a reporting principle is the same as or similar to that of the present disclosure, an improved method is also included in the present disclosure.

BRIEF DESCRIPTION OF THE DRAWINGS

Figures 5, 6:
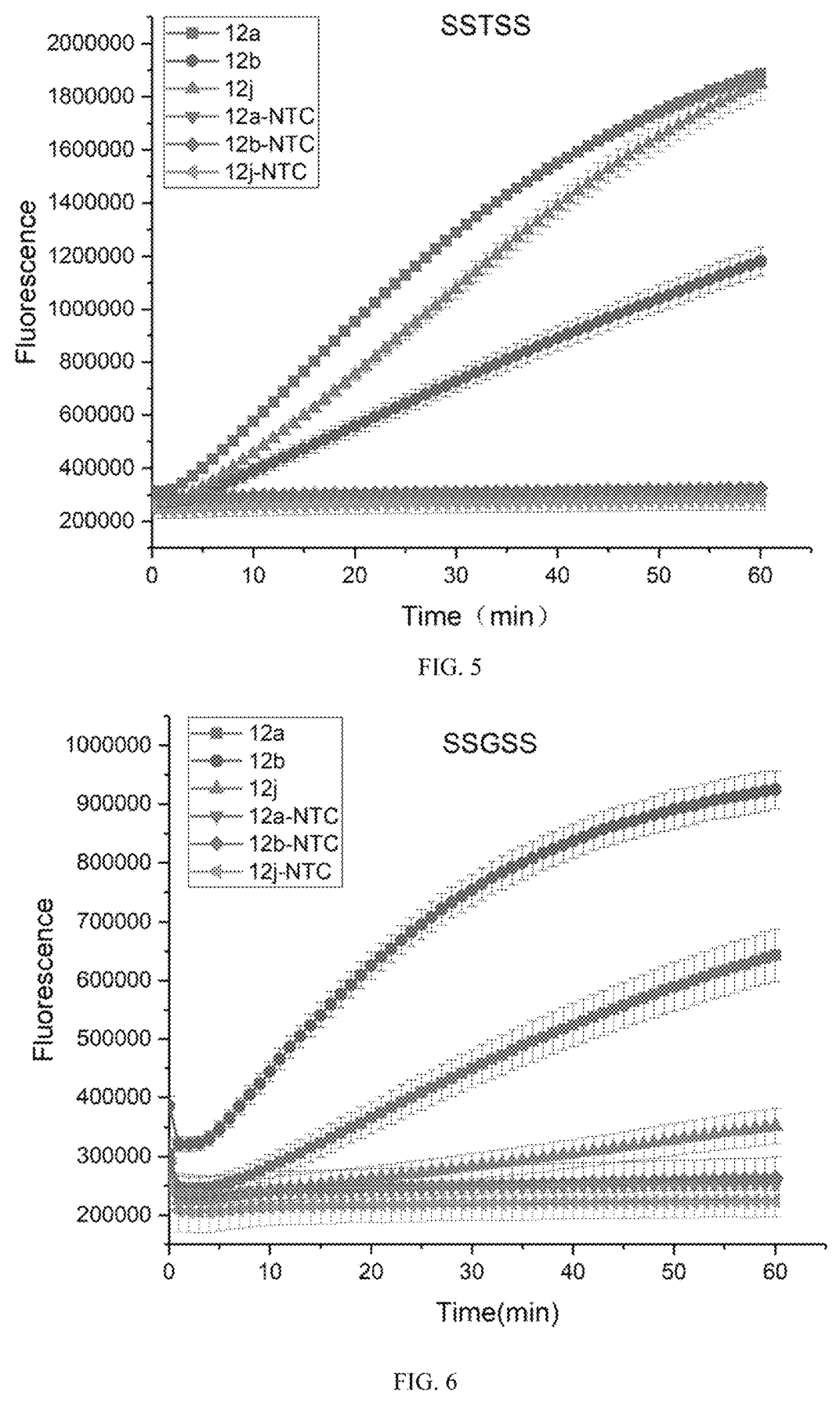

FIG. 5 shows that, when a sequence of the single-stranded nucleic acid reporter is 5'-6-FAM/S//S//T//S//S//3'-BHQ1, Cas12a and Cas12j can specifically cleave the single-stranded nucleic acid reporter and leads to better detectable signals than other proteins.

FIG. 6 shows that, when a sequence of the single-stranded nucleic acid reporter is 5'-6-FAM/S//S//G//S//S//3'-BHQ1, Cas12a and Cas12b can specifically cleave the single-stranded nucleic acid reporter and leads to better detectable signals than other proteins, where a detectable signal of Cas12b is stronger than that of Cas12a.

DETAILED DESCRIPTION OF THE EMBODIMENTS

Figure 1:
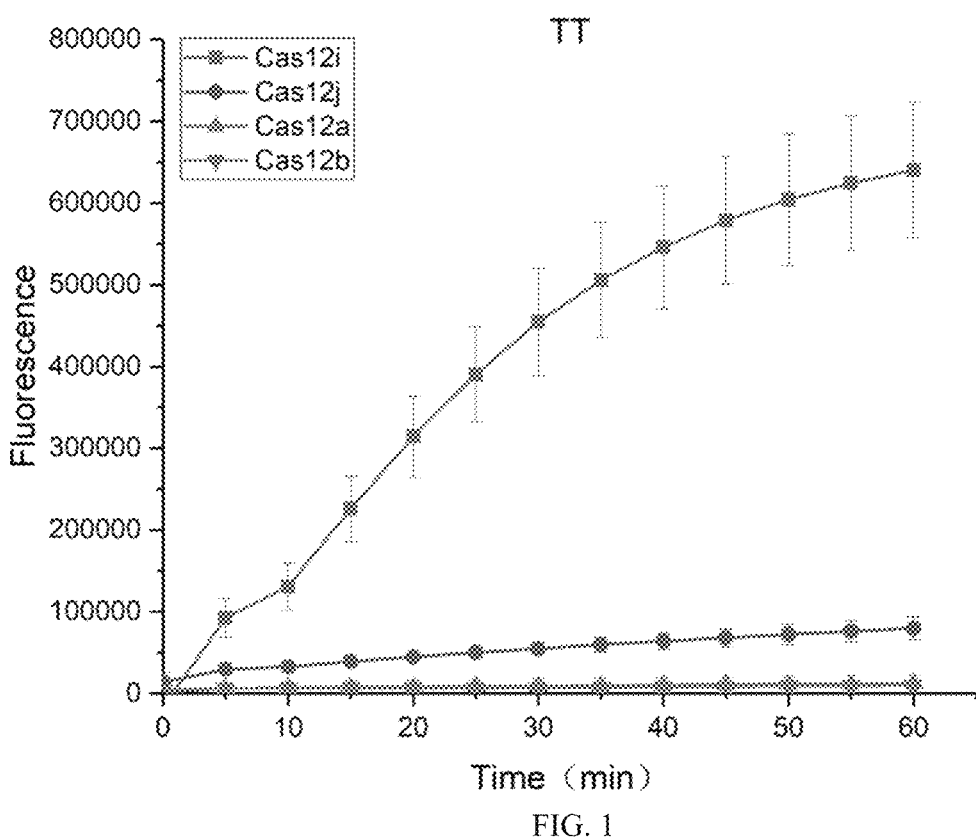
FIG. 1 shows that, when a sequence of the single-stranded nucleic acid reporter is 5'-6-FAM//T//T//3'-BHQ1, Cas12i can specifically cleave the single-stranded nucleic acid reporter and leads to a better detectable signal than other proteins.
Figure 2:
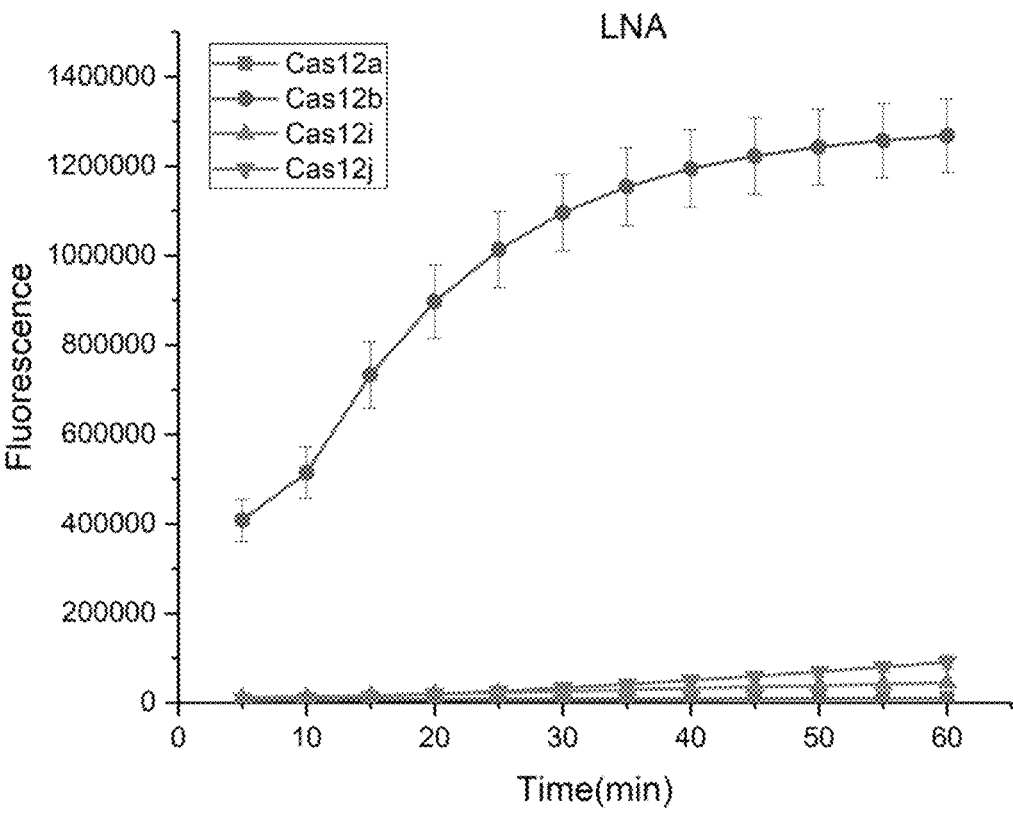
FIG. 2 shows that, when the single-stranded nucleic acid reporter is a nucleic acid analogue (LNA, sequence: 5'-6-FAM//LNA_T//LNA_T//LNA_T//LNA_T//LNA_T//3'-BHQ1, Cas12b can specifically cleave the single-stranded nucleic acid reporter and leads to a better detectable signal than other proteins.
Figure 3:
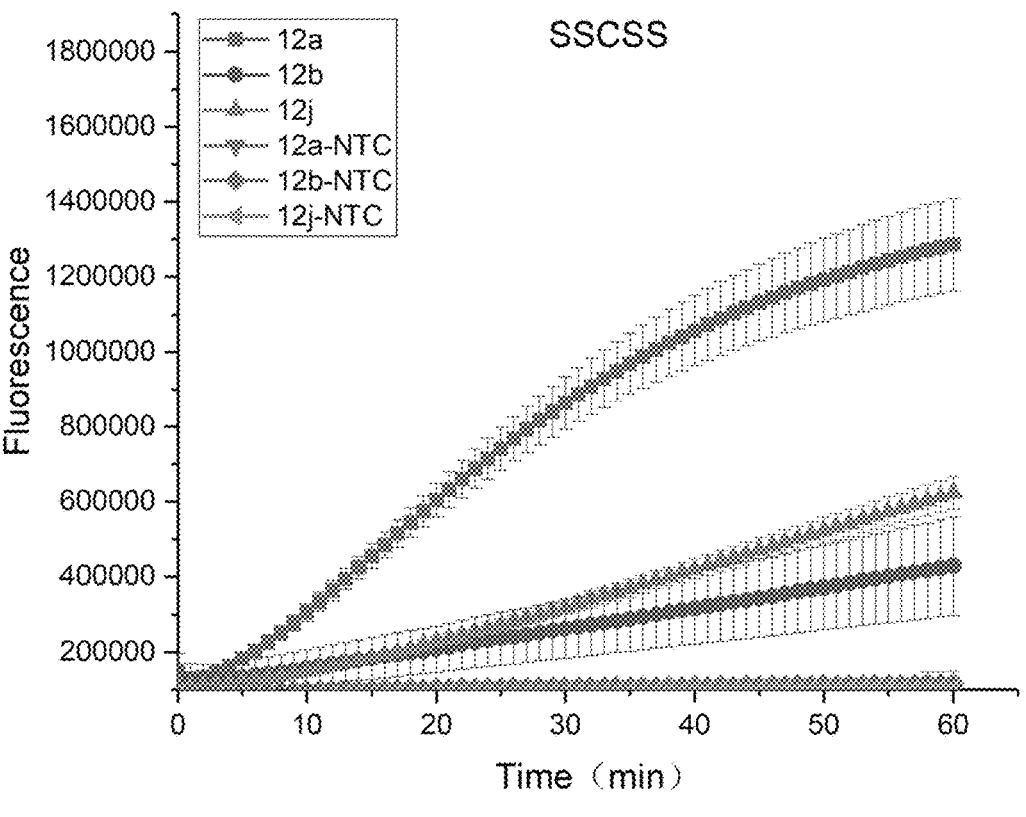
FIG. 3 shows that, when a sequence of the single-stranded nucleic acid reporter is 5'-6-FAM/S//S//C//S//S//3'-BHQ1, Cas12a can specifically cleave the single-stranded nucleic acid reporter and leads to a better detectable signal than other proteins.
Figure 4:
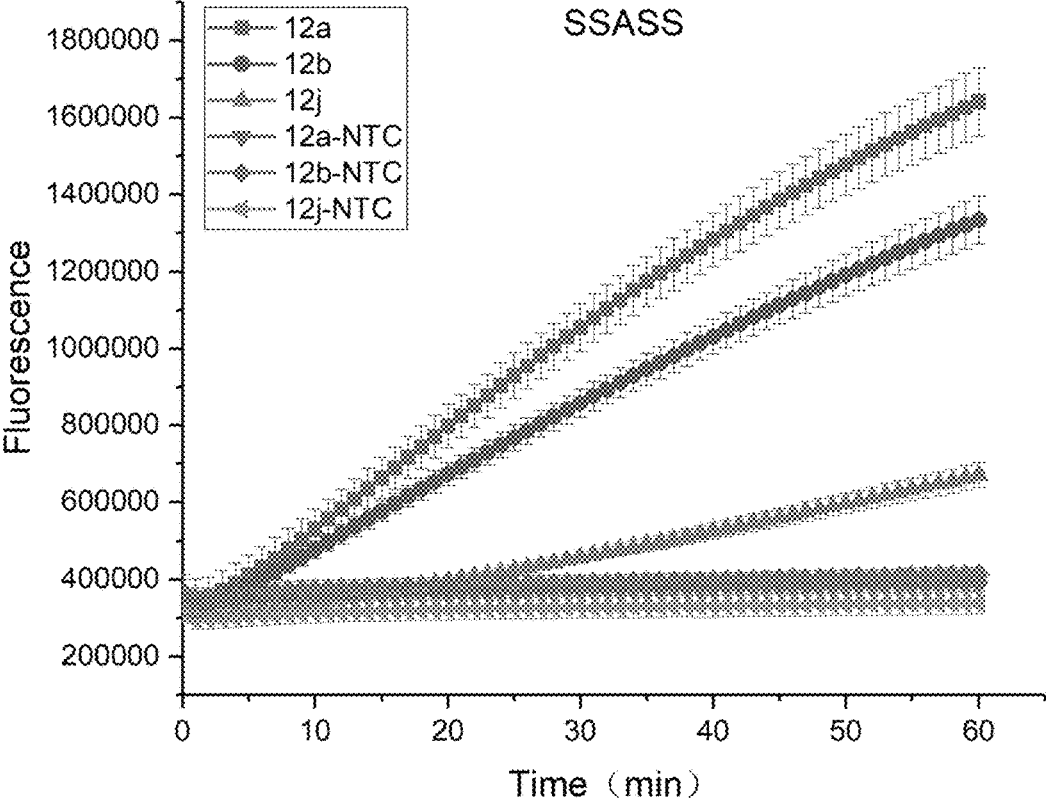
FIG. 4 shows that, when a sequence of the single-stranded nucleic acid reporter is 5'-6-FAM/S//S//A//S//S//3'-BHQ1, Cas12a and Cas12b can specifically cleave the single-stranded nucleic acid reporter and leads to better detectable signals than other proteins, where a detectable signal of Cas12a is stronger than that of Cas12b.
Figure 7:
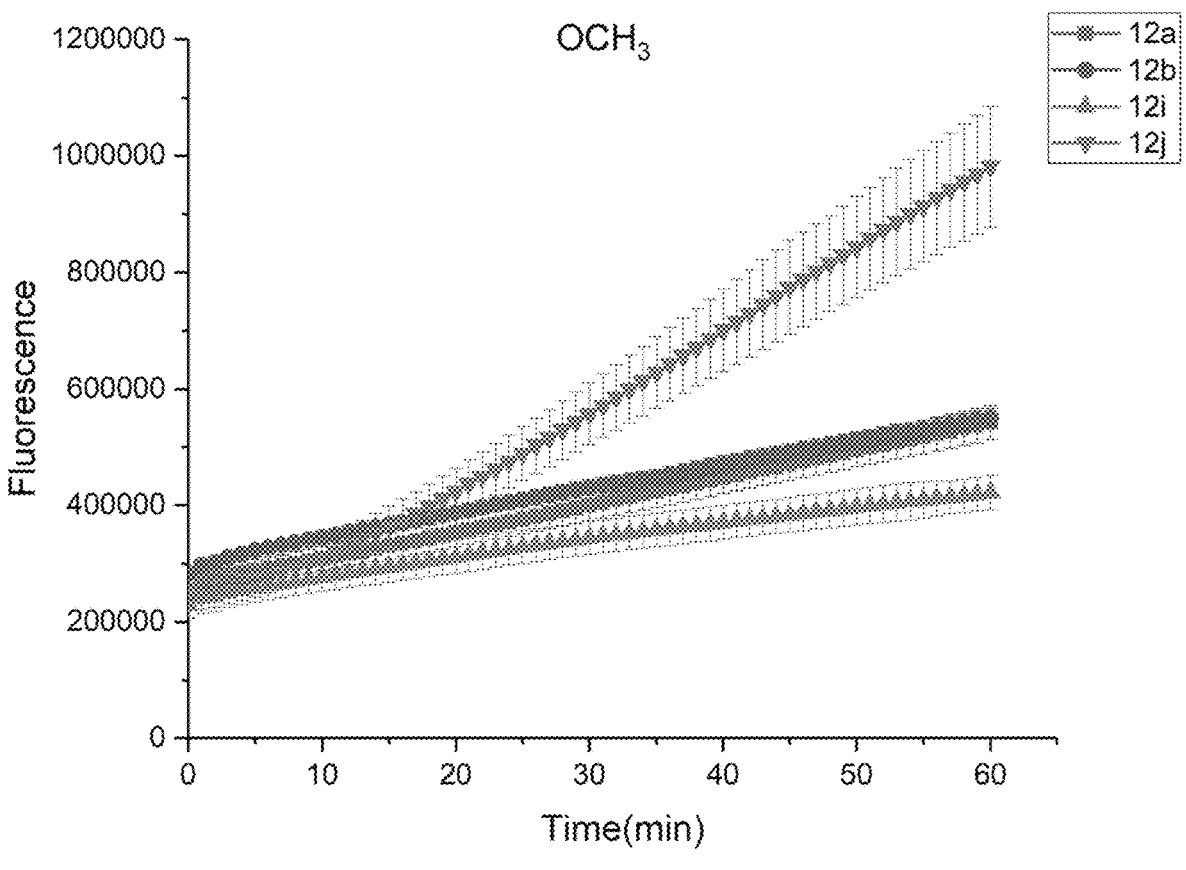
FIG. 7 shows that, when the single-stranded nucleic acid reporter is a nucleic acid analogue (2'-O-methyl RNA), Cas12j can specifically cleave the single-stranded nucleic acid reporter and leads to a better detectable signal than other proteins.

The present disclosure will be further explained below in conjunction with examples. The following examples are only preferred examples of the present disclosure, and are not intended to limit the present disclosure in other forms. Any technical personnel familiar with the profession may use the technical content disclosed above to derive equivalent examples through equivalent changes. Any simple modification or equivalent change made to the following examples according to the technical essence of the present disclosure without departing from the content of the solutions of the present disclosure shall fall within the protection scope of the present disclosure.

The technical solutions of the present disclosure are based on the following principle: a nucleic acid is extracted from a sample to be tested, for example, a target nucleic acid can be obtained through amplification; a gRNA that can be paired with the target nucleic acid is used to guide a Cas protein to recognize and bind to the target nucleic acid; then the Cas protein stimulates the cleavage activity of the single-stranded nucleic acid reporter to cleave the single-stranded nucleic acid reporter in the system; two terminals of the single-stranded nucleic acid reporter are provided with a fluorophore and a quencher respectively, and if the single-stranded nucleic acid reporter is cleaved, fluorescence will be excited; and in other embodiments, the two terminals of the single-stranded nucleic acid reporter can also be provided with a labeling molecule that can be detected by colloidal gold.

Example 1: Nucleic Acid Detection Using Cas12i, Cas12j, Cas12a, and Cas12b

In this example, different single-stranded nucleic acid reporters were designed, and Cas12i, Cas12j, Cas12a, and Cas12b were used for detection. The different single-stranded nucleic acid reporters were single-stranded nucleic acid reporter-TT, single-stranded nucleic acid reporter-TT-F, single-stranded nucleic acid reporter-LNA, single-stranded nucleic acid reporter-SSCSS, single-stranded nucleic acid reporter-SSASS, single-stranded nucleic acid reporter-SSTSS, single-stranded nucleic acid reporter-SSGSS, and single-stranded nucleic acid reporter-OCH$_3$.

A structure of the single-stranded nucleic acid reporter-TT was 5'-6-FAM//T//T//3'-BHQ1; a structure of the single-stranded nucleic acid reporter-TT-F was 5'-6-FAM//T-F//T-F//3'-BHQ1 (where T-F was 2'-fluoro-modified T); a structure of the single-stranded nucleic acid reporter-LNA was 5'-6-FAM//LNA_T//LNA_T//LNA_T//LNA_T//LNA_T//3'-BHQ1; a structure of the single-stranded nucleic acid reporter-SSCSS was 5'-6-FAM//S//S//C//S//S//3'-BHQ1 (where S was dSpacer); a structure of the single-stranded nucleic acid reporter-SSASS was 5'-6-FAM//S//S//A//S//S//3'-BHQ1 (where S was dSpacer); a structure of the single-stranded nucleic acid reporter-SSTSS was 5'-6-FAM//S//S//T//S//S//3'-BHQ1 (where S was dSpacer); a structure of the single-stranded nucleic acid reporter-SSGSS was 5'-6-FAM//S//S//G//S//S//3'-BHQ1 (where S was dSpacer); and a structure of the single-stranded nucleic acid reporter-OCH$_3$ was 5'-6-FAM//T-OCH$_3$//T-OCH$_3$//T-OCH$_3$//T-OCH$_3$//T-OCH$_3$//3'-BHQ1 (where T-OCH$_3$ was 2'-O-methyl-modified T).

The applicants verified the detection effects of Cas12a (SEQ ID NO: 1), Cas12b (SEQ ID NO: 2), Cas12i (SEQ ID NO: 3), and Cas12j (SEQ ID NO: 4) when the above-mentioned nucleic acid reporters with an abasic spacer were used, and an experimental design was as follows:

| Cas protein (final concentration: 50 nM) | Target nucleic acid (final concentration: 25 nM) | gRNA (final concentration: 50 nM) | Reporter (final concentration: 400 nM) |
|---|---|---|---|
| Cas12a | Cas12i3-g2-ssDNA0 | LbCas12a-TGW6-g1 | Single-stranded nucleic acid reporter-TT |
| Cas12b | Cas12i3-g2-ssDNA0 | AaCas12b-TGW6-g1 | Single-stranded nucleic acid reporter-TT-F |
| Cas12i | Cas12i3-g2-ssDNA0 | DRi3-gOsTGW6-2 | Single-stranded nucleic acid reporter-LNA |
| Cas12j | Cas12j19-g3-ssDNA0 | DR12j19gOsTGW6-3 | Single-stranded nucleic acid reporter-SSCSS |
| | | | Single-stranded nucleic acid reporter-SSASS |
| | | | Single-stranded nucleic acid reporter-SSTSS |
| | | | Single-stranded nucleic acid reporter-SSGSS |
| | | | Or single-stranded nucleic acid reporter-OCH3 |

A sequence of the Cas12i3-g2-ssDNA0 was shown in SEQ ID NO 5;

a sequence of the Cas12j119-g3-ssDNA0 was shown in SEQ TD NO: 6;

a sequence of the LbCas12a-TGW6-g1 was shown in SEQ ID NO: 7;

a sequence of the AaCas12b-TGW6-g1 was shown in SEQ ID NO: 8;

a sequence of the Cas12i3-TGW6-g2 was shown in SEQ ID NO: 9; and a sequence of the Cas12j19-TGW6-g3 was shown in SEQ ID NO: 10.

A content of each component in the 20 μl system was as follows:

| Component | 20 μl system consumption | Final concentration |
|---|---|---|
| Buffer | 2 ul | 1× |
| 100 mM DTT | 2 ul | 10 mM |
| 2 μM Cas12 | 0.5 ul | 50 nM |
| 1 μM gRNA | 1 ul | 50 nM |
| 100 nM ssDNA | 1 ul | 5 nM |
| 10 μM single-stranded nucleic acid reporter | 0.4 ul | 200 nM |
| H$_2$O | Up to 20 ul | |

The detection effects of each component is shown in FIGS. 1-7

When the probe sequence was TT, Cas12i could specifically cleave the single-stranded nucleic acid reporter, and resulted in a better detectable signal than other proteins.

When the probe sequence was 5'-6-FAM//T-F//T-F//3'-BHQ1, Cas12i could specifically cleave the single-stranded nucleic acid reporter, and resulted in a better detectable signal than other proteins.

In addition, when the probe sequence was CT (5'-6-FAM//C//T//3'-BHQ1), Cas12i also could specifically cleave the single-stranded nucleic acid reporter, and resulted in a better detectable signal than other Cas proteins.

When the probe was a nucleic acid analogue (LNA), Cas12b could specifically cleave the single-stranded nucleic acid reporter, and resulted in a better detectable signal than other proteins.

When the probe sequence was 5'-6-FAM/S//S//C//S//S//3'-BHQ1, Cas12a could specifically cleave the single-stranded nucleic acid reporter, and resulted in a better detectable signal than other proteins.

When the probe sequence was 5'-6-FAM/S//S//A//S//S//3'-BHQ1, Cas12a and Cas12b could specifically cleave the single-stranded nucleic acid reporter, and resulted in better detectable signals than other proteins.

When the probe sequence was 5'-6-FAM/S//S//T//S//S//3'-BHQ1, Cas12a and Cas12j could specifically cleave the single-stranded nucleic acid reporter, and resulted in better detectable signals than other proteins.

When the probe sequence was 5'-6-FAM/S//S//G//S//S//3'-BHQ1, Cas12a and Cas12b could specifically cleave the single-stranded nucleic acid reporter, and resulted in better detectable signals than other proteins, where a detectable signal of Cas12b was stronger than that of Cas12a.

When the probe was a nucleic acid analogue (2'-O-methyl RNA), Cas12j could specifically cleave the single-stranded nucleic acid reporter, and resulted in a better detectable signal than other proteins.

Example 2: Doublet Detection of Virus COVID-19 Using Cas12i and Cas12j

Cas12i and Cas12j were used to achieve the doublet detection of genes N and S of virus COVID-19: Cas12i targeted the gene S, with a reporter of 5'-6-FAM//C//T//3'-BHQ1, and the gRNA sequence was AGAGAAUGUGUG-CAUAGUCACACUCAGGAUGUUAACUGCACAG, as shown in SEQ ID NO: 11; and Cas12j targeted the gene N, with a reporter of 5'-Cy3//S//S//T//S//S//3'-BHQ2, and the gRNA sequence was GUGCUGCUGUCUCCCAGACGG-GAGGCAGAACUGCACCGCGACAUUCCGAAGAACG C, as shown in SEQ ID NO: 12.

Figure 8:
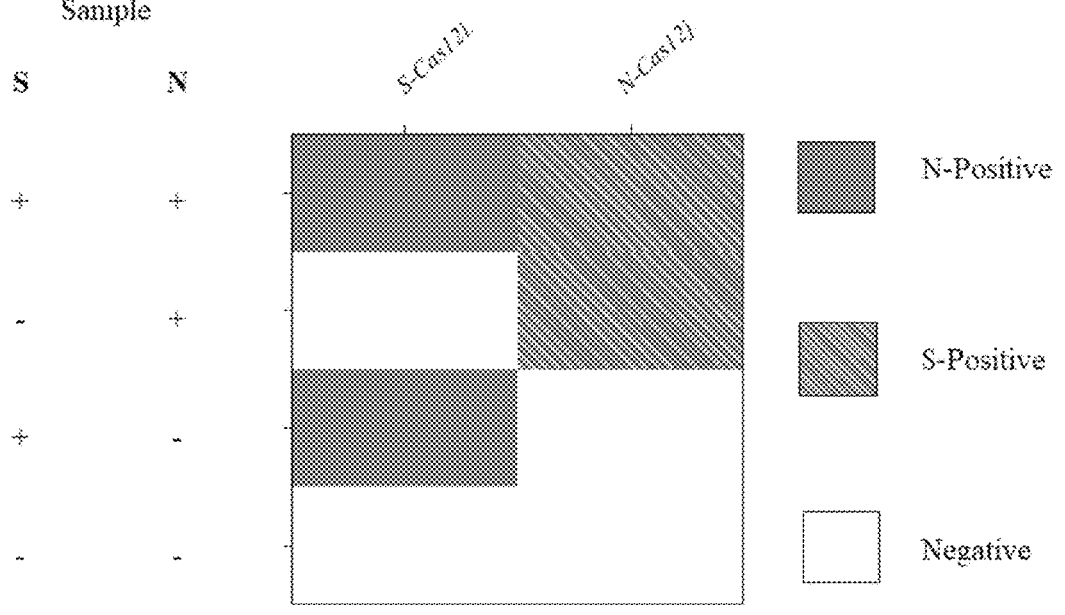
FIG. 8 shows the doublet detection of genes N and S of the virus COVID-19 with Cas12i and Cas12j, where cas12i targets the gene S, with a reporter of FAM-CT-BHQ1; cas12j targets the gene N, with a reporter of Cy3-SSTSS-BHQ2; when both genes S and N are present in a sample, two fluorescent signals can be detected; when only the gene N is present in a sample, only the FAM fluorescent signal corresponding to Cas12i can be detected; when only the gene S is present in a sample, only the Cy3 fluorescent signal corresponding to Cas12j can be detected; and when both the gene S and the gene N are not present in a sample, neither of the two signals can be detected.

As shown in FIG. 8, the results showed that, when both genes S and N were present in a sample, two fluorescent signals could be detected; when only the gene N was present in a sample, only the FAM fluorescent signal corresponding to Cas12i could be detected; when only the gene S was present in a sample, only the Cy3 fluorescent signal corresponding to Cas12j could be detected; and when both the gene S and the gene N were not present in a sample, neither of the two signals could be detected.

Example 3: Triplet Detection of Different Target Nucleic Acids Using Cas12a, Cas12b, and Cas12i Cas12a, Cas12b, and Cas12i were used to achieve the triplet detection of different target nucleic acids.

| Cas protein | Target gene name | Reporter sequence | Fluorophore |
|---|---|---|---|
| cas12a | EV71 VP1 | 5'6-FAM//A//S//S//T//3'BHQ1 | FAM |
| cas12b | OsTGW6 | 5'TAMRA//LNA-T//LNA-T//LNA-T//LNA-T//LNA-T//3'BHQ2 | TAMRA |
| cas12i | COVID-19 orf1ab | 5'HEX//C//T//3'BHQ1 | HEX | cas12a targeted the target nucleic acid EV71 VP1 with a sequence of GTGCACGCAACAAAAGTGAACTCTG-CATCAAAGCGCATGT (SEQ ID NO: 13), the single-stranded nucleic acid reporter was 5'-6-FAM//A//dS//dS//T//3'-BHQ1 (where dSpacer was an abasic spacer), and the gRNA was LbCas12a-g71-1 with a sequence of UAAUUUCUACUAAGUGUAGAUAUGCAGAGUUCA-CUUUUGUUGCG (SEQ ID NO: 14, where the bolded part was a position for the gRNA to bind to the protein, and the underlined part was a position matching the target nucleic acid sequence).

Cas12b targeted the target nucleic acid OsTGW6 with a sequence of GATCGTTGGTAGTTCATGCTGCTGTCG GTGAAATAAACATCTCCGGTAAC (SEQ ID NO: 15), the single-stranded nucleic acid reporter was 5'-TTAMRA//LNA-T//LNA-T//LNA-T//LNA-T//LNA-T//3'-BHQ2 (where LNA-T refers to an LNA with a base of T), the tracrRNA sequence was GUCUAAAGGACA GAAU UUUUCAACGGGUGUGCCAAUGGCCACUUUCCAG-GUGGC AAAGCCCGUUGAACUUCUCAAAAAGAA CGCUCGCUCAGUGUUCUGAC (SEQ ID NO: 16), and the crRNA sequence was GUCGGAUCACUGAGCGA GCGAUCUGAGAAGUGGCAC<u>uuucaccgacagcagcauga</u> (SEQ ID NO: 17, where the underlined part was a position matching the target nucleic acid sequence).

Cas12i targeted the target nucleic acid COVID-19 orf1ab with a sequence of Ggcaccaaattccaaaggtttaccttggtaat-catcttcagtaccatactcatattgag (SEQ ID NO: 18), the single-stranded nucleic acid reporter was 5'-HEX//C//T//3'-BHQ1, and the gRNA was CV19-Lamb-i3g5g with a sequence of AGAGAAUGUGUGCAUAGUCACAC<u>ccaaggUaaacc-UUUggaaUUUgg</u> (SEQ ID NO: 19, where the bolded part was a position for the gRNA to bind to the protein, and the underlined part was a position matching the target nucleic acid sequence).

Figure 9:
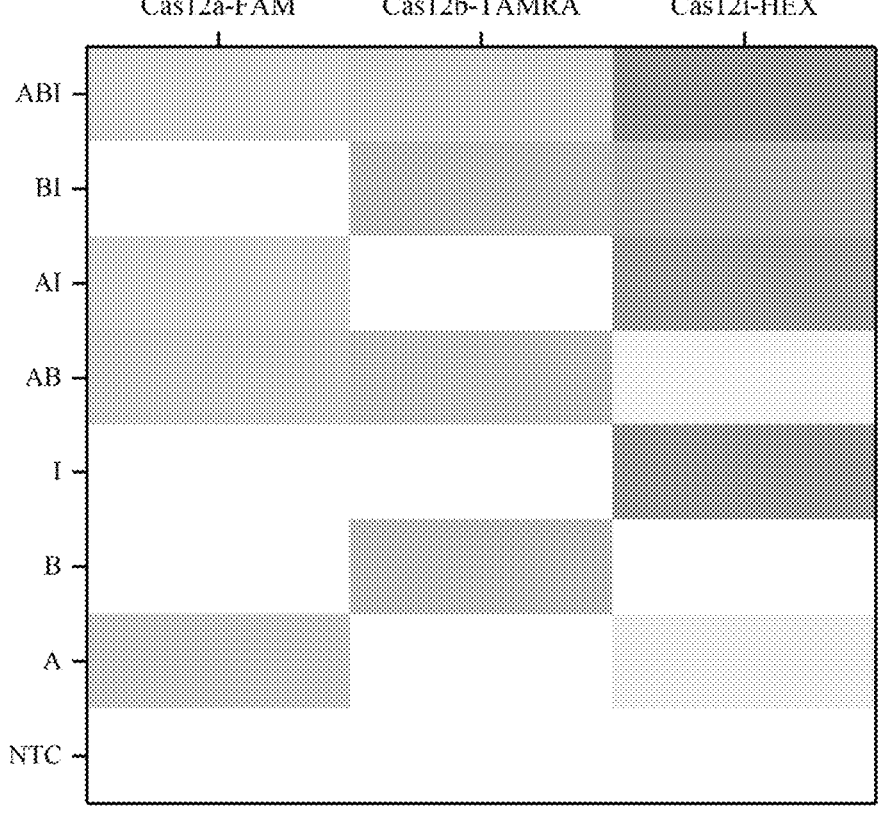
FIG. 9 shows the triplet detection of different target nucleic acids with Cas12a, Cas12b, and Cas12i.
Figure 9:
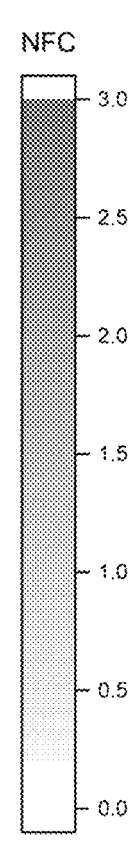

As shown in FIG. 9, the left side of the figure shows a target nucleic acid added to the system, which is expressed in an abbreviation of a corresponding enzyme (for example, "ABI" refers to the target nucleic acid EV71 VP1 detected by the Cas12a (A) protein added to the system, the target nucleic acid OsTGW6 detected by the Cas12a (B) protein, and the target nucleic acid COVID-19 orf1ab detected by the Cas12i (I) protein; and the upper side of the figure shows a fluorescent signal generated after the Cas protein in this system recognizes a target nucleic acid, then activates the bypass cleavage activity, and specifically cleaves the single-stranded nucleic acid reporter (for example, "Cas12-FAM" refers to an FAM fluorescence intensity generated after the Cas12 protein in this system recognizes the target nucleic acid EV71 VP1, then activates the bypass cleavage activity, and specifically cleaves the single-stranded nucleic acid reporter 5'-6-FAM//A//S//S//T//3'-BHQ1). The darker the color, the stronger the signal.

Specifically, for example, in the first row, when the target nucleic acid EV71 VP1 detected by the Cas12a (A) protein, the target nucleic acid OsTGW6 detected by the Cas12b (B) protein, and the target nucleic acid COVID-19 orf1ab detected by the Cas12i (I) protein are added to the system, FAM fluorescence corresponding to Cas12a, TAMRA fluorescence corresponding to Cas12b, and HEX fluorescence corresponding to Cas12i can be detected.

The test results prove that Cas12a, Cas12b, and Cas12i show different preferences for single-stranded nucleic acid reporters and thus can be used for triplet nucleic acid detection.

All documents mentioned in the present disclosure are cited as references in this application, as if each document was individually cited as a reference. In addition, it should be understood that after reading the above teaching content of the present disclosure, those skilled in the art can make various changes or modifications to the present disclosure, and these equivalents shall also fall within the scope defined by the appended claims of the present application.

What is claimed is:

1. A method for detecting a target nucleic acid in a sample, comprising contacting the sample with at least three nucleic acid detection compositions; and detecting a detectable signal generated due to a cleavage of the Cas protein on the single-stranded nucleic acid reporter to detect the target nucleic acid;

wherein the at least three nucleic acid detection compositions comprises at least three compositions selected from the group consisting of:

a first nucleic acid detection composition comprising Cas12i, a gRNA, and a first single-stranded nucleic acid reporter;

a second nucleic acid detection composition comprising Cas12b, a gRNA, and a second single-stranded nucleic acid reporter;

a third nucleic acid detection composition comprising Cas12a, a gRNA, and a third single-stranded nucleic acid reporter; and a fourth nucleic acid detection composition comprising Cas12j, a gRNA, and a fourth single-stranded nucleic acid reporter;

wherein, the first single-stranded nucleic acid reporter comprises at least two consecutive nucleotides selected from the group consisting of ribonucleotides, deoxyribonucleotides, nucleic acid analogues and combinations thereof;

the second single-stranded nucleic acid reporter comprises at least one nucleotide and at least one abasic spacer or a locked nucleic acid (LNA);

the third single-stranded nucleic acid reporter comprises at least one nucleotide and at least one abasic spacer; and the fourth single-stranded nucleic acid reporter comprises at least one nucleotide and at least one abasic spacer or 2'-O-methyl RNA.

2. The method according to claim 1, wherein the nucleic acid detection composition comprises any three or four from the group consisting of the first nucleic acid detection composition, the second nucleic acid detection composition, the third nucleic acid detection composition, and the fourth nucleic acid detection composition.

3. The method according to claim 1, wherein the detectable signal is detected by a visual-based detection, a sensor-based detection, a color detection, a gold nanoparticle-based detection, a fluorescence polarization, a colloidal phase transition, an electrochemical detection, or a semiconductor-based detection.

4. The method according to claim 1, wherein the target nucleic acid comprises ribonucleotides or deoxyribonucleotides; and the target nucleic acid comprises a single-stranded nucleic acid or a double-stranded nucleic acid.

5. The method according to claim 1, wherein a 5' terminus and a 3' terminus of each single stranded nucleic acid reporter comprise different reporter groups or different labeling molecules.

6. The method according to claim 1, wherein the target nucleic acid is a viral nucleic acid sequence, a bacterial nucleic acid sequence or a disease related nucleic acid sequence.

7. The method according to claim 1, wherein the method further comprises extracting the target nucleic acid from the sample.

8. A system or composition or kit for detecting a target nucleic acid in a sample, comprising at least three nucleic acid detection compositions selected from the group consisting of:

i) a first nucleic acid detection composition comprising Cas12i, a gRNA, and a first single-stranded nucleic acid reporter;

ii) a second nucleic acid detection composition comprising Cas12b, a gRNA, and a second single-stranded nucleic acid reporter;

iii) a third nucleic acid detection composition comprising Cas12a, a gRNA, and a third single-stranded nucleic acid reporter; and iv) a fourth nucleic acid detection composition comprising Cas12j, a gRNA, and a fourth single-stranded nucleic acid reporter;

wherein, the first single-stranded nucleic acid reporter comprises at least two consecutive nucleotides selected from the group consisting of ribonucleotides, deoxyribonucleotides, nucleic acid analogues and combinations thereof;

the second single-stranded nucleic acid reporter comprises i) at least one nucleotide and at least one abasic spacer; or, ii) a locked nucleic acid (LNA);

the third single-stranded nucleic acid reporter comprises at least one nucleotide and at least one abasic spacer; and the fourth single-stranded nucleic acid reporter comprises i) at least one nucleotide and at least one abasic spacer; or, ii) 2'-O-methyl RNA.

9. The system or composition or kit according to claim 8, wherein any of the at least one abasic spacer is independently selected from the group consisting of dSpacer, Spacer C3, Spacer C6, Spacer C12, Spacer9, Spacer 12, Spacer 18, Inverted Abasic Site, and rAbasic Site.

10. The system or composition or kit according to claim 8, wherein the system or composition or kit is configured for detecting the target nucleic acid in the sample.

11. The method according to claim 2, wherein the detectable signal is detected by a visual-based detection, a sensor-based detection, a color detection, a gold nanoparticle-based detection, a fluorescence polarization, a colloidal phase transition, an electrochemical detection, or a semiconductor-based detection.

12. The method according to claim 2, wherein a 5' terminus and a 3' terminus of the single-stranded nucleic acid reporter are provided with different reporter groups, respectively; or, the 5' terminus and the 3' terminus of the single-stranded nucleic acid reporter are provided with different labeling molecules, respectively.

13. The method according to claim 3, wherein a 5' terminus and a 3' terminus of the single-stranded nucleic acid reporter are provided with different reporter groups, respectively; or, the 5' terminus and the 3' terminus of the single-stranded nucleic acid reporter are provided with different labeling molecules, respectively.

14. The method according to claim 4, wherein a 5' terminus and a 3' terminus of the single-stranded nucleic acid reporter are provided with different reporter groups, respectively; or, the 5' terminus and the 3' terminus of the single-stranded nucleic acid reporter are provided with different labeling molecules, respectively.

15. The method according to claim 2, wherein the method further comprises extracting the target nucleic acid from the sample.

16. The method according to claim 3, wherein the method further comprises extracting the target nucleic acid from the sample.

17. The method according to claim 4, wherein the method further comprises extracting the target nucleic acid from the sample.

18. The method according to claim 5, wherein the method further comprises extracting the target nucleic acid from the sample.

19. The method according to claim 6, wherein the method further comprises extracting the target nucleic acid from the sample.

20. The system or composition or kit according to claim 9, wherein the system or composition or kit is configured for detecting the target nucleic acid in the sample.

* * * * *